US006841345B1

(12) United States Patent
Hone et al.

(10) Patent No.: US 6,841,345 B1
(45) Date of Patent: *Jan. 11, 2005

(54) TREATMENT AND PREVENTION OF IMMUNODEFICIENCY VIRUS INFECTION BY ADMINISTRATION OF NON-PYROGENIC DERIVATIVES OF LIPID A

(75) Inventors: David M. Hone, Ellicott City, MD (US); Richard Crowley, Gaithersburg, MD (US); George Lewis, Baltimore, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/383,709

(22) Filed: Aug. 26, 1999

Related U.S. Application Data

(62) Division of application No. 08/938,106, filed on Sep. 26, 1997, now Pat. No. 6,368,604.

(51) Int. Cl.[7] .............................................. C12Q 1/70
(52) U.S. Cl. ......................... 435/5; 435/7.2; 435/7.32; 435/7.37; 435/41; 435/252.33; 424/241.1; 514/54
(58) Field of Search ..................................... 424/282.1

(56) References Cited

U.S. PATENT DOCUMENTS

| 5,158,939 A | 10/1992 | Takayama et al. ............. 514/53 |
| 5,189,674 A | 2/1993 | Shimizu |
| 5,191,072 A | 3/1993 | Hasegawa et al. ........... 536/117 |
| 5,510,119 A | 4/1996 | Santus et al. ................ 424/490 |
| 5,593,969 A | 1/1997 | Kamireddy et al. ........... 514/25 |
| 5,597,573 A | 1/1997 | Kamireddy et al. ..... 424/234.1 |
| 5,997,881 A | 12/1999 | Powell et al. |

FOREIGN PATENT DOCUMENTS

| AL | WO 97/08955 | 3/1997 |
| AL | WO97/18837 | 5/1997 |
| AM | WO95/23156 | 8/1995 |
| AT | WO 91/16449 | 10/1991 |
| AT | WO92/00101 | 1/1992 |
| AT | WO92/06113 | 4/1992 |
| AT | WO94/21292 | 9/1994 |
| CA | WO97/25061 | 7/1997 |
| CH | WO84/04526 | 11/1984 |
| EP | 0 437 016 A2 | 7/1991 |
| EP | 0 536 969 A2 | 4/1993 |
| EP | 0 668 289 A1 | 8/1995 |
| GB | 2 220 211 A | 1/1990 |
| JP | A-63010728 | 1/1998 |

OTHER PUBLICATIONS

Cornelis, P., et al., 1992, "Stability, frequency and multiplicity of transposon insertions in the pyoverdine region in the chromosomes of different fluorescent pseudomonads", J. Gen. Microbiol. 138:1337–1343.*

Pries, A, et al., 1992, "Identification of a lipoamide dehydrogenase gene as second locus affected in poly(3–hydroxybutryic acid)–leaky mutants of *Alcaligenes eutrophus*", FEMS Microbiol. Lett. 97:227–234.*

Öberg, B. and L. Vrang, 1990, "Screening for new agents", Eur. J. Clin. Microbiol. Infect. Dis. 9(7):466–471.*

Yarchoan, R. and S. Broder, 1992, "Correlations between the in vitro and in vivo activity of anti–HIV agents: implications for future drug development", J. Enzym. Inhib. 6:99–111.*

Gait, M. and J. Karn, 1995, "Progress in anti–HIV structure–based drug design.", TIBTECH 13(10):430–438.*

Flexner, C. and C. Hendrix, 1997, "Pharmacology of antiretroviral agents.", in *AIDS: Biology, Diagnosis, Treatment and Prevention, fourth edition,* DeVita, Jr., V., et al., eds., Lippincott–Raven Publishers, pp. 479–493.*

Pomerantz, R. J., et al., 1990, "Lipopolysaccharide is a potent monocyte/macrophage–specific stimulator of human immunodeficiency virus type 1 expression", J. Exp. Med. 172:253–261.*

Moriuchi, H., et al., 2000, "In vitro reactivation of human immunodeficiency virus 1 from latently infected, resting CD4[+] T cells after bacterial stimulation", J. Infect. Dis. 181(6):2041–4, (abstract provided).*

Verani et al., "C–C Chemokines Released by Lipopolysaccharide (LPS)–Stimulated Human Macrophages Suppress HIV–1 Infection in Both Macrophages and T–Cells", J. of Exp. Med. 185(5):805–816 (Mar. 1997).

Baker et al., "Structural Features that Influence the Ability of Lipid A and its Analogues to Abolish Expression of Suppressor T–Cell Activity", Infect. Immun. 60(7):2694–2701 (1992).

Clementz et al., "Function of the *Escherichia coli* msbB Gene, a Multicopy Suppressor of htrB Knockouts, in the Acylation of Lipid A", J. Biol. Chem. 272:10353–10360 (1997).

(List continued on next page.)

*Primary Examiner*—Laurie Scheiner
*Assistant Examiner*—Jeffrey S. Parkin
(74) *Attorney, Agent, or Firm*—Marianne Fuierer; Steven J. Hultquist; Yongzhi Yang

(57) ABSTRACT

The present inventors have found that certain preparations containing LPS and/or lipid A variants, derivatives, and/or analogs demonstrate non-pyrogenic properties and exhibit anti-viral activities. In particular, non-pyrogenic preparations of LPS, lipid A, LPS antagonists and lipid A antagonists, and derivatives thereof induce β chemokine secretion, such as MIP-1β, but not proinflammatory cytokines, such as TNFα, IL-1β and IL-6. Non-pyrogenic preparations of the invention have been demonstrated by the Applicant to suppress HIV replication in human peripheral blood monocytes, as described by way of example herein. The present invention provides preparations of LPS or lipid A variants, analogs and derivatives of decreased or absent pyrogenicity which can be used as therapeutics for the treatment or prevention of immunodeficiency virus infection and its consequences.

17 Claims, 7 Drawing Sheets

OTHER PUBLICATIONS

Figure 1:
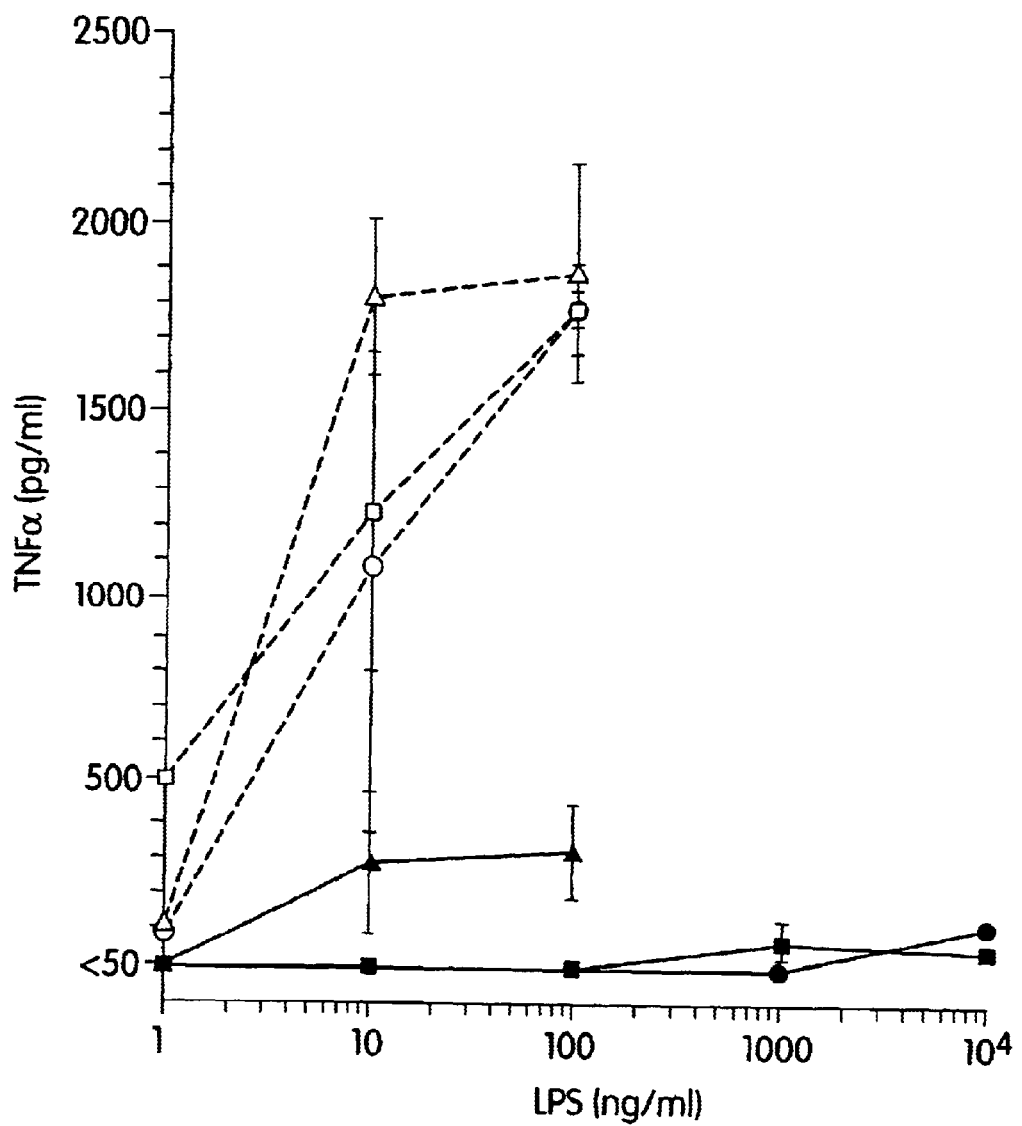

Clementz et al., "Function of the htrB High Temperature Requirement Gene of *Escherichia coli* in the Acylation of Lipid A", J. Biol. Chem. 271:12095–12102 (1996).
Golenback et al., "Lipid X Protects Mice against Fatal *Escherichia coli* Infection", Infect. Immun. 56(4)779–784 (1988).
Karow et al., "Complex Phenotypes of Null mutations in the htr genes, whose products aare essential for *Escherichia coli* growth at elevated temperatures""Research in Microbiology" 142:289–294 (1991).
Kotani et al., "Immunobiological Activities of Synthetic Lipid A Analogues with Low Endotoxicity", Infect. Immun. 54(3):673–682 (1986).
Lee et al., "Mutations of the htrB Locus of *Haemophilus influenzae* Nontypable Strain 2019 is Associated with Modifications of Lipid A and Phosphorylation of the Lipo–oligosaccharide", J. Bio. Chem. 270:27151–27159 (1995).
Nowotny, A., "Review of the Molecular Requirements of Endotoxic Actions", Rev. Infect. Dis. 9(5):S503–S511 (1987).
Ogawa et al., Chemical Abstract No. 163524, "Disaccharide Derivatives as Analgesics", vol. 1098, No. 19, Nov. 7, 1988.
Polissi et al., "Mutational analysis and properties of the msbA gene of *Escherichia coli*, coding for an essential ABC family transporter", Mol. Micro 20:1221–1233 (1996).
Pugliese, C. et al., "Relationships Between the Structure and Function of Lipopolysaccharide Chemotypes with Regard to their Effects on the Human Polymorphonuclear Neutrophil", Molec. Immunol. 25(7):631–637 (1988).
Schnailman et al., "Genetics of lipopolysaccharide Biosynthesis in Enteric Bacteria", Microbiol. Rev. 57:655–682 (1993).
Somerville et al., "A Novel *Escherichia coli* Lipid A Mutant that produces an Antiinflammatory Lipopolysaccharide", J. Clin. Invest. 97:359–365 (1996).
Sunshine et al., "Mutation of the htrB Gene in a Virulent *Salmonella typhimorium* by Intergeneric Transduction: Strain Construction and Phenotype Characterization", J. Bacteri. 179:5521–5533 (1997).
Zhou et al., "Function of *Escherichia coli* MsbA, and Essential ABC Family Transporter, in Lipid A and Phospholipid Biosynthesis", J. Biol. Chem. 273:12466–12475 (1988).
Johnson et al., "Characterization of a Nontoxic Monophosphoryl Lipid A", Reviews of Infectious Diseases 9 (5): S512–S516 (1987).
Friedman et al., "Immunoadjuvanticity of Endotoxins and Nontoxic Derivatives for Normal and Leukemic Immunocytes", Advances in Experimental Medicine and Biology 256:525–535 (199).
Bernstein, et al., 1991, J. Clinical invest. 88:540.
Begrasra, et al., 1992, Proc. Natl. Acad. Sci 89:6285.
Bhat et al., Glyco Biology 2:535–539 (1992).
Bunnell et al., Crit. Care Med. Suppl. 23:147 (1995).
Bunnell et al., Crit. Care Med. Suppl. 23:A151 (1995).
Chemical Abstracts, vol. 109, No. 17, Nov. 7, 1988, Abstract No. 163524, "Disaccharide Derivatives as Analgesics".
Christ et al., J. Am. Chem. Soc. 116:3637 (1994).
Darveau et al., "Ability of Bacteria Associated With Chronic Inflammatory Disease to Stimulate E–Selectin Expression and Promote Neutrophil Adhesion", Infect. And Immun. 63:1311–1317 (1995).
Erwin and Munford, J. Biol. Chem. 256:16444 (1990).
Fagan et al., J. Immunol. 153:5230 (1994).
Flexner, C. and C. Hendrix, 1997, "Pharmacology of anti-retroviral agents," in AIDS: Biology, Diagnosis, Treatment and Prevention, fourth edition, DeVita, J., V., et al., eds., Lippincott–Raven Publishers, pp. 479–493.
Friedman et al., "Immunodeficiency of Endotoxins and Nontoxic Derivatives for Normal and Leukemic Immunocytes" Advances in Exp. Med. and Biol., vol. 256, (1990) pp. 525–535.
Gait, M. and J. Karn, 1995, "Progress in anti–Hiv structure–based drug design," TIBTECH 13(10):430–438.
Golenback et al., J. Biol. Cehm. 266:19490 (1991).
International Search Report dated Mar. 17, 1999, for PCT/US98/20264, filed Sep. 28, 1998.
Johnson et al., "Characterization of a Nontoxic Monophosphoryl Lipid A," Review of Infectious Diseases, vol. 9, No. S5 (1987) pp. S512–S516.
Karow et al., J. Bacteriol., 173:741–750 (1991).
Karow et al., "Isolation and Characterization of the *Escherischia coli* msbB Gene, a Multicopy Suppressor of Null Mutations in the High–Temperature Requirement Gene htrB," J. Bacteriology, 174:702–710 (1992).
Karow et al., "The Lethal Phenotpye Caused by Null Mutations in the *Escherichia coli* htrB Gene is Suppressed by Mutations in the accBC Operon, Encoding Two Subunits of Acetyl Coenzyme A Carbohydrate," J. Bacteriol. 174:7407 (1992).
Kornbluth et al., J. Exp. Medicine 169:1137 (1989).
Kotani et al., Infect. Immun. 49:225 (1985).
Kovach et al., J. Exp. Med. 172:77–84 (1990).
Munford and Hall, J. Biol. Chem. 264:15613 (1989).
Neter et al., J. Immunol. 76:377 (1956).
Öberg, B. and L. Vrang, 1990, "Screening for new agents," Eur. J. Clin. Microbiol. Infect. Dis. 9(7):466–471.
Perera et al., Infect. Immun 61:2015 (1993).
Qureshi et al., J. Biol. Chem. 263:5502 (1988).
Qureshi et al., J. Biol. Chem. 266:6532 (1991).
Raetz et al., J. Bacteriol. 175:5745–5753 (1993).
Rietschal et al., FASEB J. 8:217–225 (1994).
Salimath et al., Eur. J. Biochem. 136:195 (1983).
Sica et al., J. Exp. Med. 185:969 (1997).
Ulmer et al., Infect Immun. 60(12):5145–5152 (1992).
Wang et al., Infect. Immun. 59(12):4655–4664 (1991).
Yarchoan, R. and S. Broder, 1992, "Correlations between the in vitro and in vivo activity of anti–HIV agents: implications for future drug development," J. Enzym, Inhib. 6:99–111.

\* cited by examiner

TREATMENT AND PREVENTION OF IMMUNODEFICIENCY VIRUS INFECTION BY ADMINISTRATION OF NON-PYROGENIC DERIVATIVES OF LIPID A

This is a division of application Ser. No. 08/938,106, filed Sep. 26, 2003 now U.S. Pat. No. 6,368,604.

1. FIELD OF THE INVENTION

The present invention relates to lipopolysaccharide (LPS) or lipid A variants, derivatives, and analogs with non-pyrogenic and non-endotoxic properties as well as methods for treatment and prevention of immunodeficiency virus infection, in particular HIV infection, using these LPS or lipid A variants and analogs and derivatives. The present invention also relates to LPS and lipid A antagonists and their use as therapeutics in the treatment and prevention of HIV infection. The LPS and lipid A variants, derivatives, and analogs of the present invention preferably induce the secretion of β chemokines but exhibit decreased induction relative to LPS and lipid A of secretion of proinflammatory cytokines, such as IL-1β, IL-6 and TNF-α. The present invention further relates to pharmaceutical compositions for the treatment and prevention of HIV infection.

2. BACKGROUND OF THE INVENTION

2.1. The Human Immunodeficiency Virus

The human immunodeficiency virus (HIV) has been implicated as the primary cause of the slowly degenerative immune system disease termed acquired immune deficiency syndrome (AIDS) (Barre-Sinoussi, F., et al., 1983, *Science* 220:868–870; Gallo, R., et al., 1984, *Science* 224:500–503). There are at least two distinct types of HIV: HIV-1 (Barre-Sinoussi, F., et al., 1983, *Science* 220:868–870; Gallo, R., et al., 1984, *Science* 224:500–503) and HIV-2 (Clavel, F., et al., 1986, *Science* 233:343–346; Guyader, M., et al., 1987, *Nature* 326:662–669). Further, a large amount of genetic heterogeneity exists within populations of each of these types. In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich, N., et al., 1984, *RNA Tumor Viruses*, Weiss, R., et al., eds., CSH-Press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, *Science* 240:1427–1439). The HIV viral particle comprises a viral core, composed in part of capsid proteins, together with the viral RNA genome and those enzymes required for early replicative events. Myristylated gag protein forms an outer shell around the viral core, which is, in turn, surrounded by a lipid membrane envelope derived from the infected cell membrane. The HIV envelope surface glycoproteins are synthesized as a single 160 kilodalton precursor protein which is cleaved by a cellular protease during viral budding into two glycoproteins, gp41 and gp120. gp41is a transmembrane glycoprotein and gp120 is an extracellular glycoprotein which remains non-covalently associated with gp41, possibly in a trimeric or multimeric form (Hammarskjold, M., & Rekosh, D., 1989, *Biochem. Biophys. Acta* 989:269–280).

HIV is targeted to $CD4^+$ cells because a CD4 cell surface protein (CD4) acts as the cellular receptor for the HIV-1 virus (Dalgleish, A., et al., 1984, *Nature* 312:763–767; Klatzmann et al., 1984, *Nature* 312:767–768; Maddon et al., 1986, *Cell* 47:333–348). Viral entry into cells is dependent upon gp120 binding the cellular CD4 receptor molecules (McDougal, J. S., et al., 1986, *Science* 231:382–385; Maddon, P. J., et al., 1986, *Cell* 47:333–348), explaining HIV's tropism for $CD4^+$ cells, while gp41 anchors the envelope glycoprotein complex in the viral membrane. While these virus:cell interactions are necessary for infection, there is evidence that additional virus:cell interactions are also required.

2.2. HIV Treatment

HIV infection is pandemic and HIV-associated diseases represent a major world health problem. Although considerable effort is being put into the design of effective therapeutics, currently no curative anti-retroviral drugs against AIDS exist. In attempts to develop such drugs, several stages of the HIV life cycle have been considered as targets for therapeutic intervention (Mitsuya, H., et al., 1991, *FASEB J.* 5:2369–2381). Many viral targets for intervention with HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2',3'-dideoxynucleoside analogs such as AZT, ddI, ddC, and d4T have been developed which have been shown to been active against HIV (Mitsuya, H., et al., 1991, *Science* 249:1533–1544).

The new treatment regimens for HIV-1 show that a combination of anti-HIV compounds, which target reverse transcriptase (RT), such as azidothymidine (AZT), lamivudine (3TC), dideoxyinosine (ddI), dideoxycytidine (ddC) used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson, A. S., et al., 1996, *Science* 15:1582–1586). However, it is likely that long-term use of combinations of these chemicals will lead to toxicity, especially to the bone marrow. Long-term cytotoxic therapy may also lead to suppression of $CD8^+$ T cells, which are essential to the control of HIV, via killer cell activity (Blazevic, V., et al., 1995, *AIDS Res. Hum. Retroviruses* 11:1335–1342) and by the release of suppressive factors, notably the chemokines Rantes, MIP-1a and MIP-1β (Cocchi, F., et al., 1995, *Science* 270:1811–1815). Another major concern in long-term chemical anti-retroviral therapy is the development of HIV mutations with partial or complete resistance (Lange, J. M., 1995, *AIDS Res. Hum. Retroviruses* 10:S77–82). It is thought that such mutations may be an inevitable consequence of anti-viral therapy. The pattern of disappearance of wild-type virus and appearance of mutant virus due to treatment, combined with coincidental decline in $CD4^+$ T cell numbers strongly suggests that, at least with some compounds, the appearance of viral mutants is a major underlying factor in the failure of AIDS therapy.

Attempts are also being made to develop drugs which can inhibit viral entry into the cell, the earliest stage of HIV infection. Here, the focus has thus far been on CD4, the cell surface receptor for HIV. Recombinant soluble CD4, for example, has been shown to inhibit infection of $CD4^+$ T cells by some HIV-1 strains (Smith, D. H., et al., 1987, *Science*

238:1704–1707). Certain primary HIV-1 isolates, however, are relatively less sensitive to inhibition by recombinant CD4 (Daar, E., et al., 1990, *Proc. Natl. Acad. Sci. USA* 87:6574–6579). In addition, recombinant soluble CD4 clinical trials have produced inconclusive results (Schooley, R., et al., 1990, *Ann. Int. Med.* 112:247–253; Kahn, J. O., et al., 1990, *Ann. Int. Med.* 112:254–261; Yarchoan, R., et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, *Science* 249:527–533).

Recently, chemokines produced by $CD8^+$ T cells have been implicated in suppression of HIV infection (Paul, W. E., 1994, *Cell* 82:177; Bolognesi, D. P., 1993, *Semin. Immunol.* 5:203). The chemokines RANTES, MIP-1α and MIP-1β, which are secreted by $CD8^+$ T cells, were shown to suppress HIV-1 p24 antigen production in cells infected with HIV-1 or HIV-2 isolates in vitro (Cocchi, F, et al., 1995, *Science* 270:1811–1815). These chemokines, alone or in combination, effectively suppressed the replication of several primary isolates of HIV-1, HIV-2 and SIV when tested in a variety of in vitro assays (Cocchi et al. supra). The mechanism of chemokine-mediated suppression was further delineated by a series of independent reports showing that β chemokine suppression CCR5 serves as a co-receptor for macrophage-tropic NSI isolates of HIV (Alkhatib et al., 1996, *Science* 272:1955; Dragic et al., 1996, *Nature* 381:667; Choe et al., 1996, *Cell* 85:1135; Berson et al., 1996, J. Virology 70:6288). However, this activity is highly specific since β chemokines blocked macrophage tropic NSI isolates but had no significant effect on T cell-tropic SI isolates of HIV-1 (Cocchi et al., supra; Alkhatib et al., supra). Thus, these and other chemokines may prove useful in therapies for some strains of HIV infection. The clinical outcome, however, of all these and other candidate drugs is still in question.

Attention is also being given to the development of vaccines for the treatment of HIV infection. The HIV-1 envelope proteins (gp160, gp120, gp41) have been shown to be the major antigens for anti-HIV antibodies present in AIDS patients (Barin et al., 1985, *Science* 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See for example, Ivanoff, L., et al., U.S. Pat. No. 5,141,867; Saith, G., et al., PCT International Publication No. WO92/22,654; Shafferman, A., PCT International Publication No. WO91/09,872; Formoso, C., et al., PCT International Publication No. WO90/07,119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

2.3. Lipopolysaccharides

Endotoxins of gram-negative microorganisms fulfill a vital function for bacterial viability, and induce in mammalians potent pathophysiological effects. Chemically, they are lipopolysaccharides consisting of an O-specific chain, a core oligosaccharide, and a lipid component, termed lipid A. The latter determines the endotoxic activities and together with the core constituent 3-deoxy-D-manno-octulosonic acid (KDO), essential functions for bacteria.

Under normal conditions, lipopolysaccharide (LPS) is inserted in the outer surface of the outer membrane of gram negative bacteria (Schnaitman and Klena, *Microbiol Rev*, 57:655–682 (1993)); and Makela and Stocker, In: *Handbook of endotoxin volume* 1, Elsevier Biomedical Press, Amsterdam, Rietschel (ed), pp. 59–137 (1984). Complete or "smooth" LPS is composed of three main domains called lipid A, the O-antigen (also called the O-polysaccharide) and the core region, which creates an oligosaccharide link between lipid A and the O antigen (Schnaitman and Klena, supra; and Makela and Stocker, supra). The O-antigen is composed of oligosaccharide repeat units. The structure and number of these repeats varies depending on the bacterial species and growth conditions, typically ranging from one to fifty repeats (Schnaitman and Klena, supra; and Makela and Stocker, supra). Some bacterial generi, such as Neisseria spp., produce LPS that has low numbers of O-antigen repeats and therefore is referred to as lipoligosaccharide (LOS) simply to reflect this fact (Schnaitman and Klena, supra; and Makela and Stocker, supra).

The biological properties of LPS have been extensively investigated (Rietschel et al, *FASEB J*, 8:217–225 (1994); and Raetz, *J Bacteriol*, 175:5745–5753 (1993)). This molecule has powerful pyrogenic properties and in humans purified LPS (at doses of 200 ng to 1 μg) has been shown to induce febrile responses (Greisman and Homick, *J Immunol*, 109:1210–1215 (1972); Greisman and Homick, *J Infect Dis*, 128:257–263 (1973); Abernathy and Spink, *J Clin Invest*, 37:219–225 (1958); Rietschel et al, supra; and Raetz, supra (1993)). These febrile responses are mediated by host proinflammatory cytokines IL-1, IL-6, and TNF-α, the secretion of which is induced by LPS (Rietschel et al, supra and Raetz, supra).

The biologically active component of LPS is lipid A (Rietschel et al, supra; Verma et al, *Infect Immun*, 60(6):2438–2444 (1992); Alving, *J Immunol Meth*, 140:1–13 (1991); Alving and Richards, *Immunol Lett*, 25:275–280 (1990); and Richard et al, *Infect Immun*, 56:682–686 (1988)). Activity analysis of lipid A biosynthesis precursors or synthetic intermediates showed that various elements of lipid A are essential for pyrogenicity (Rietschel et al, supra; Raetz, supra).

For several years, it has been known that under certain circumstances, stimulation with bacterial LPS protects macrophages from HIV infection (Kornbluth et al., 1989, J. Exp. Medicine 169:1137; Bernstein et al., 1991, J. Clinical Invest. 88:540; Bagasra et al., 1992, Proc. Natl. Acad. Sci. 89:6285). LPS-mediated suppression is thought to be dependent on LPS-CD14 interactions (Bagasra et al. supra), the induction of β chemokines MIP-1α, MIP-1β and RANTES (Verani et al., 1997, J. Exp. Med. 185:805) and down regulation of β chemokine receptors (Sica et al, 1997, J. Exp. Med. 185:969).

In attempts to detoxify the effects of LPS or lipid A in the treatment of Gram-negative bacteremia and septic shock, antibodies have been designed which detoxify the endotoxin activity by hydrolyzing the LPS or lipid A to products with reduced toxicity (see U.S. Pat. No. 5,597,573, issued Jan. 28, 1997).

LPS and lipid A are potent activators of proinflammatory cytokines, which accounts for the pyrogenic nature of these molecules. LPS has been shown to suppress HIV replication. LPS-induced suppression of HIV may be mediated through induction and/or down regulation of chemokine receptors. However, due to the toxicity of this molecule, LPS and lipid A are not viable candidates for the treatment of HIV.

Citation of references hereinabove shall not be construed as an admission that such references are prior art to the present invention.

3. SUMMARY OF THE INVENTION

The present inventors have found that certain preparations containing LPS and/or lipid A variants, derivatives, and/or analogs demonstrate non-pyrogenic properties and exhibit anti-viral activities, particularly anti-HIV activities. In particular, non-pyrogenic preparations of LPS, lipid A, LPS antagonists and lipid A antagonists, and derivatives thereof induce β chemokine secretion, such as MIP-1α and MIP-1β, but not proinflammatory cytokines, such as TNFα, IL-1β and IL-6. The non-pyrogenic preparations of the invention, have been demonstrated by the Applicant to suppress HIV replication in human peripheral blood monocytes, as described by way of example herein. The present invention provides preparations of reduced or substantially negligible pyrogenicity of LPS variants and lipid A variants, and analogs and derivatives thereof which may be used as therapeutics for the treatment of human immunodeficiency virus infection.

The present invention also encompasses synthetic lipid A and LPS antagonists, such as, but not limited to, lipid X and lipid $IV_A$, which suppress immunodeficiency virus replication, in particular, HIV-1 replication, and exhibit decreased induction relative to LPS and lipid A of proinflammatory cytokines such as IL-6, TNFα and IL-1β. The lipopolysaccharide compositions of the present invention include those antagonists, derivatives or analogs of LPS and lipid A which exhibit reduced pyrogenicity and proinflammatory activity relative to wild-type LPS and lipid A, respectively, yet stimulate β chemokine secretion and inhibit HIV replication. The present invention fills a tremendous need for a non-toxic, long-term treatment of HIV infection and its sequelae, ARC and AIDS.

In particular, the present invention relates to LPS or lipid A preparations isolated from gram negative organisms containing at least one mutation from the group kdsA, kdsB, htrB, msbB. In a preferred embodiment of the present invention, non-pyrogenic LPS is isolated from the *E. coli* htrB1::Tn10 msbB::Ωcam double mutant MLK986.

The present invention further relates to preparations of LPS or lipid A which have been differentially modified to yield reduced pyrogenicity or, preferably, substantially non-pyrogenic properties of the preparation relative to wild-type LPS and lipid A, respectively. In specific embodiments, preparations are treated by alkaline hydrolysis or acyloxyacyl hydrolase. Modified derivatives also in accordance with the present invention are derived from the group of monophosphoryl lipid A, penta-acyl lipid A, lipid $IV_A$ or lipid X. The present invention still further relates to LPS or lipid A derived from deacylation, by treatment with an alkali.

The present invention further relates to therapeutic methods and compositions for treatment and prevention of diseases and disorders associated with HIV-1 infection based on LPS or lipid A derivatives and therapeutically and prophylactically effective preparations containing a derivative of LPS or lipid A, and related analogs. Non-pyrogenic derivatives of lipid A and LPS can be identified by their failure to elicit a toxic response in mammals, their lack of proinflammatory activity, and/or their lack of induction of secretion of significant levels of pyrogenic cytokines, including IL-1β, IL-6 and TNFα. Preferably, non-pyrogenic derivatives are used in the therapeutic methods and compositions of the invention; alternatively, derivatives of reduced pyrogenicity relative to wild-type LPS and lipid A may be employed.

The invention provides for the treatment and prevention of HIV infection by administration of a therapeutic compound of the invention. The therapeutic compounds of the present invention include: lipid A or LPS derived from gram negative organisms containing at least one mutation selected from the group kdsA, kdsB, htrB, msbB, and derivatives and analogs of he foregoing; preparations of lipid A or LPS which have been modified to have reduced pyrogenic properties, including but not limited to, the group of monophosphoryl lipid A, penta-acyl lipid A or lipid A or LPS derivatives derived by deacylation of lipid A or LPS, treatment of LPS and lipid A with acyloxyacl hydroxylase or by treatment with an alkali, and derivatives and analogs of the foregoing. The invention also provides in vitro and in vivo assays for assessing the efficacy of therapeutics of the invention for treatment or prevention of HIV. The invention also provides pharmaceutical compositions and methods of administration of therapeutics of the invention for treatment or prevention of HIV infection.

3.1. Definitions

As used herein, the following terms shall have the meanings indicated.

| | |
|---|---|
| AIDS | Acquired Immune Deficiency Syndrome |
| ARC | AIDS-Related Complex |
| KS | Kaposi's Sarcoma |
| OI | Opportunistic Infection |
| PBMC | Peripheral Blood Mononuclear Cell |

4. DESCRIPTION OF THE FIGURES

FIG. 1. Proinflammatory Activity of W3110 LPS and Mutant Derivative MLK986 LPS. LPS was extracted from *E. coli* strain W3110 and a htrB1::Tn10, msbB::Ωcam double mutant (MLK986) after being cultured at a 30° C., 37° C. or 42° C. To characterize the proinflammatory activity of LPS harvested from W3110 and MLK986, the level of TNFα in culture supernatants was measured 8 hrs after stimulation of human PBMCs. Significant levels of TNFα secretion was observed by the parent strain W3110 LPS at concentrations above 1 mg/ml irrespective of culture temperature. In contrast, LPS from mutant strain MLK986 cultured at 30° C. only moderately elicited TNFα secretion and LPS derived from MLK986 cultured at 37° C. and 42° C. even at concentrations as high as 1 μg/ml did not elicit TNFα secretion in the human PBMC activation assay. Figure Legend:

--◯--W/42
--▫--W/37
--▵--W/30
--●--MLK/42
--■--MLK/37
--▲--MLK/30

Figure 2:
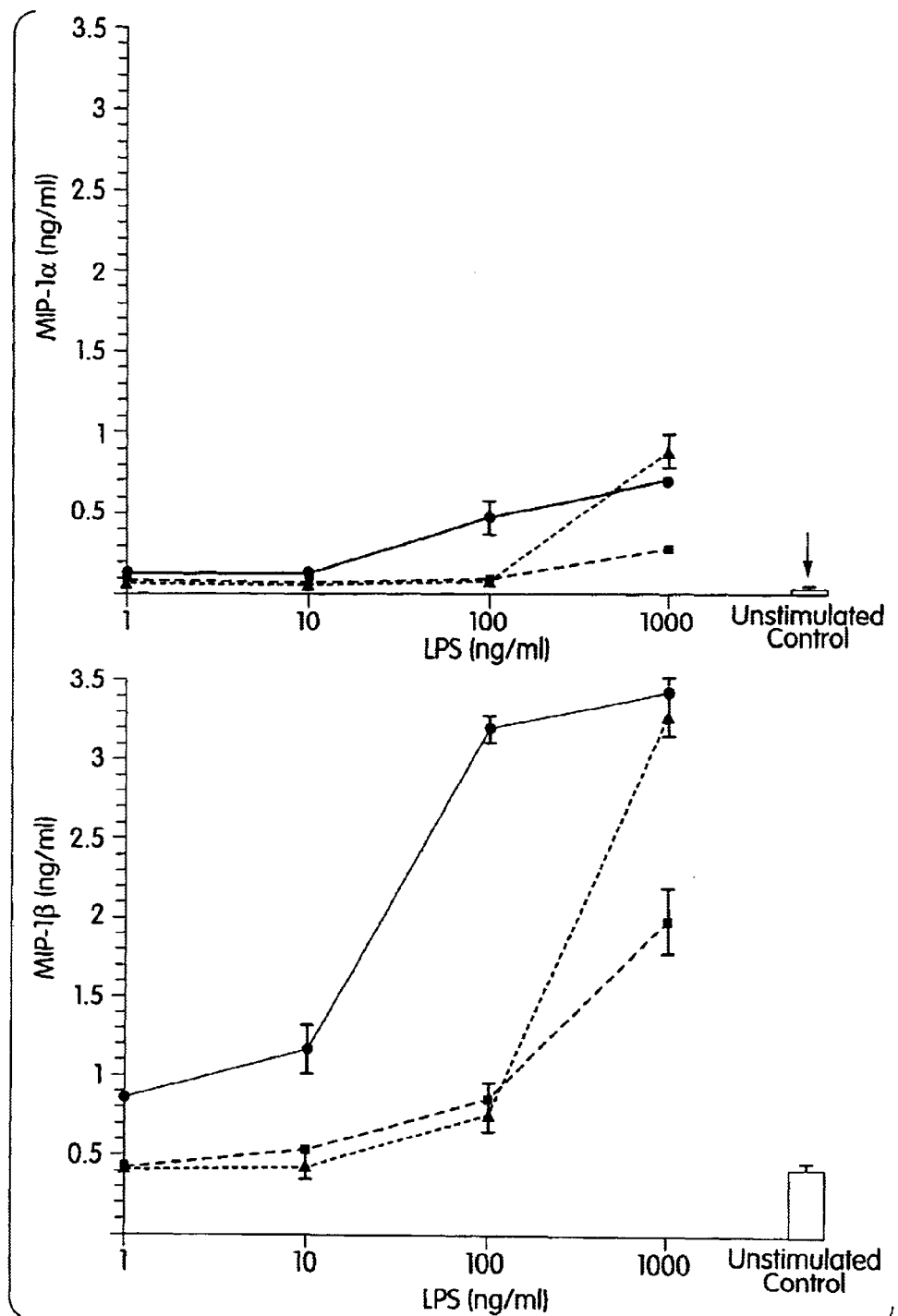

FIG. 2. LPS From MLK986 Stimulates β Chemokine Secretion. LPS isolated from MLK986, cultured at either 37° C. or 42° C., and RsDPLA stimulated the secretion of MIP-1α and MIP-1β from human PBMCs in a dose-dependent manner. Figure Legend:

—●—MLK986/37

—■—MLK986/42

--▲--RsDPLA

Figure 3:
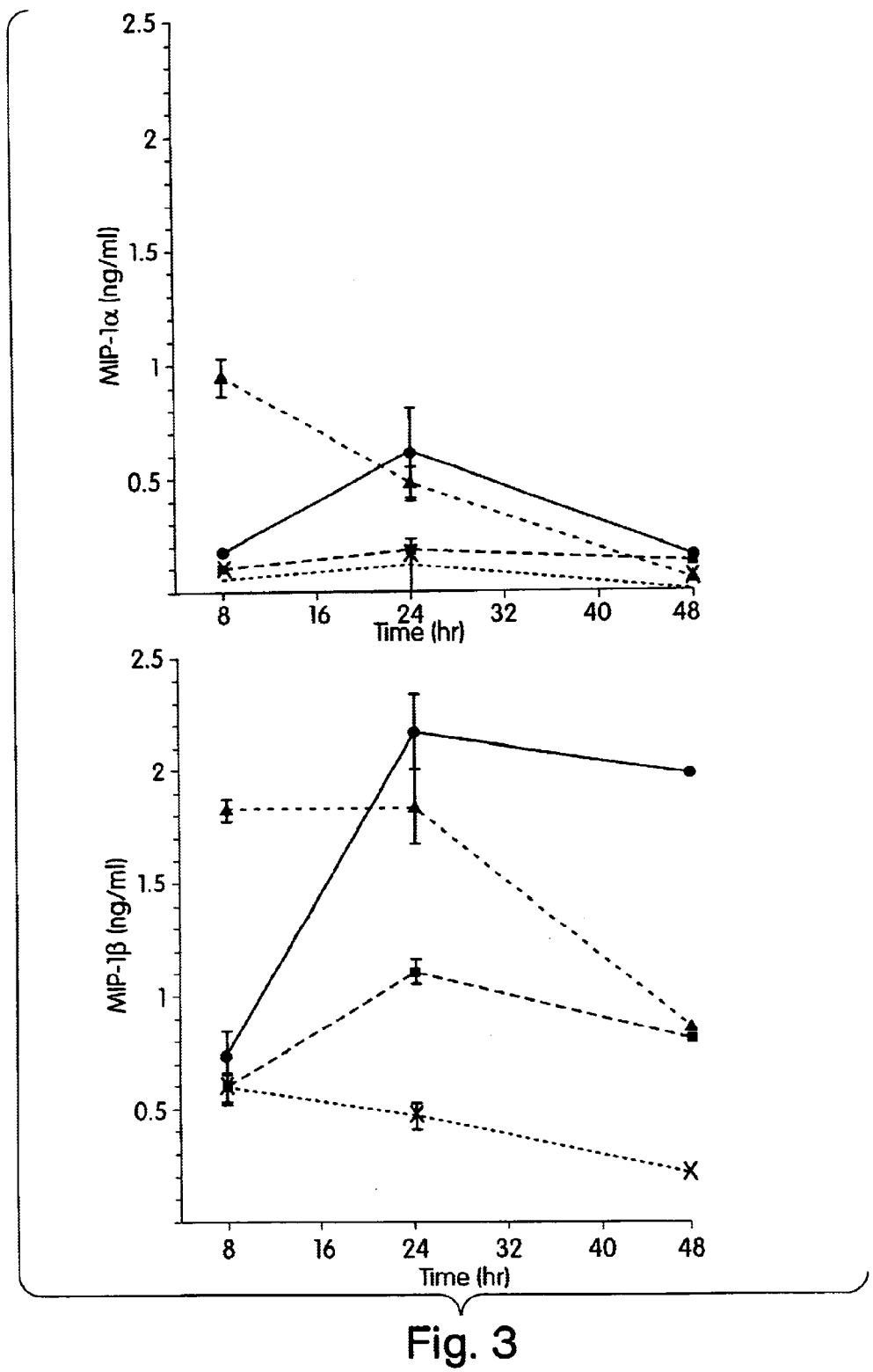

FIG. 3. The Peak Production of Chemokines Occurred 24 Hours After MLK986 Stimulation. The peak stimulation of chemokine production from human PBMCs by LPS isolated from MLK986, cultured at either 37° C. or 42° C., and RsDPLA occurred at 24 hours. The level of RANTES was not significantly elevated after stimulation with MLK986 LPS or RsDPLA. Figure Legend:

—●—MLK986/37

- ■ -MLK986/42

--▲--RsDPLA

...X...Unstimulated

Figure 4A:
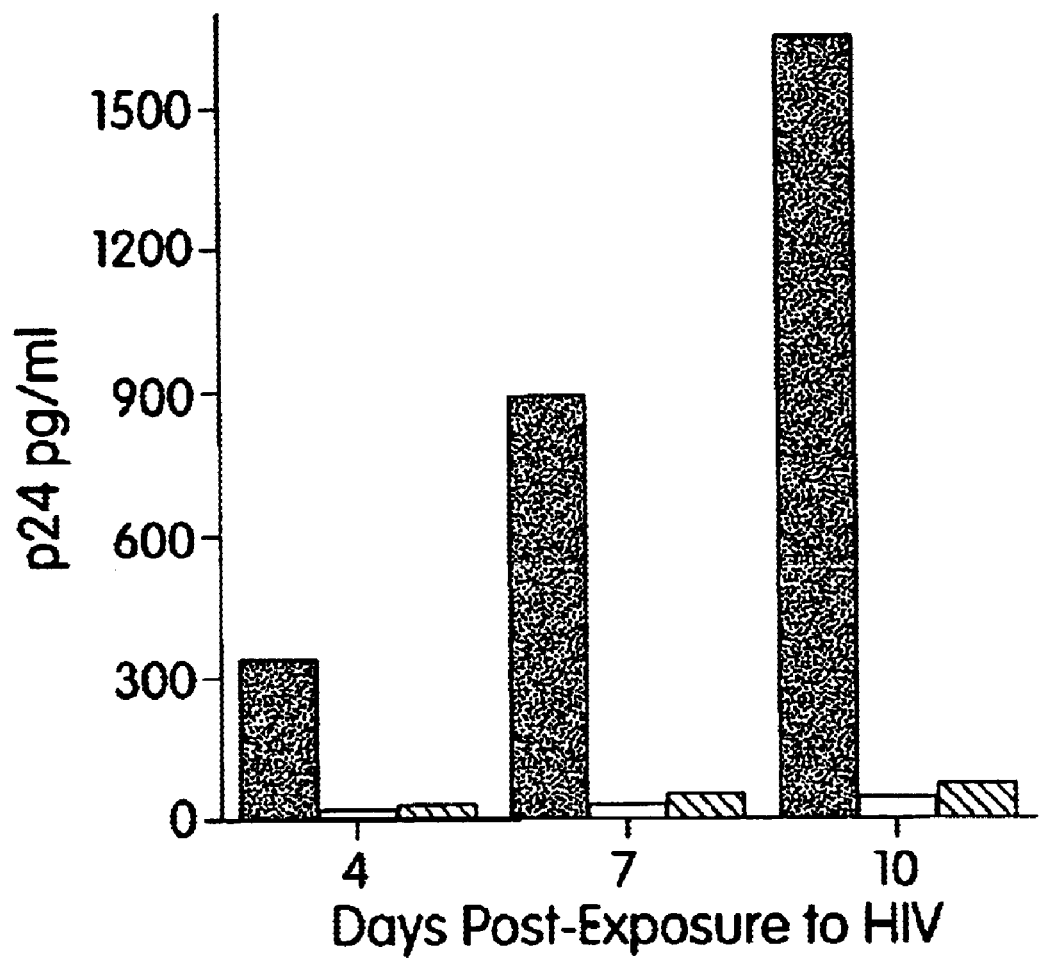
Figure 4B:
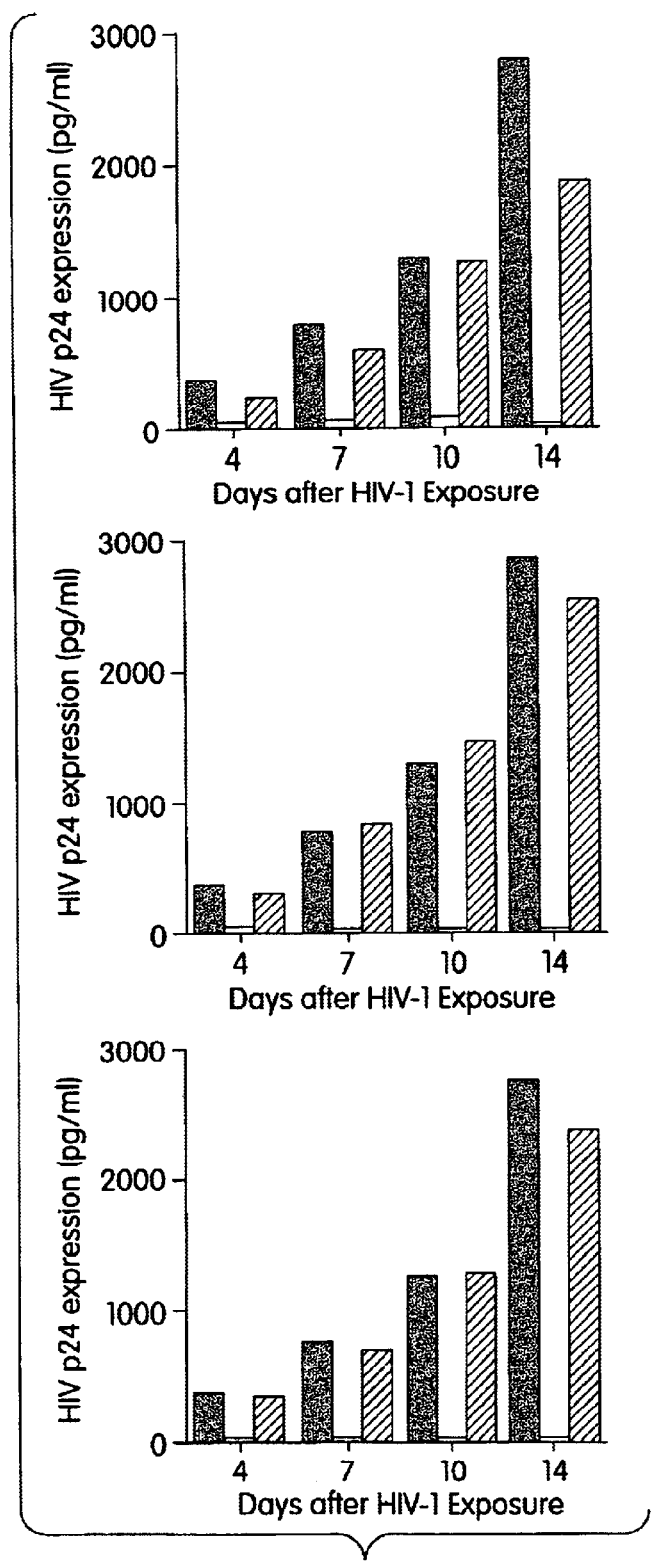
Figure 4C:
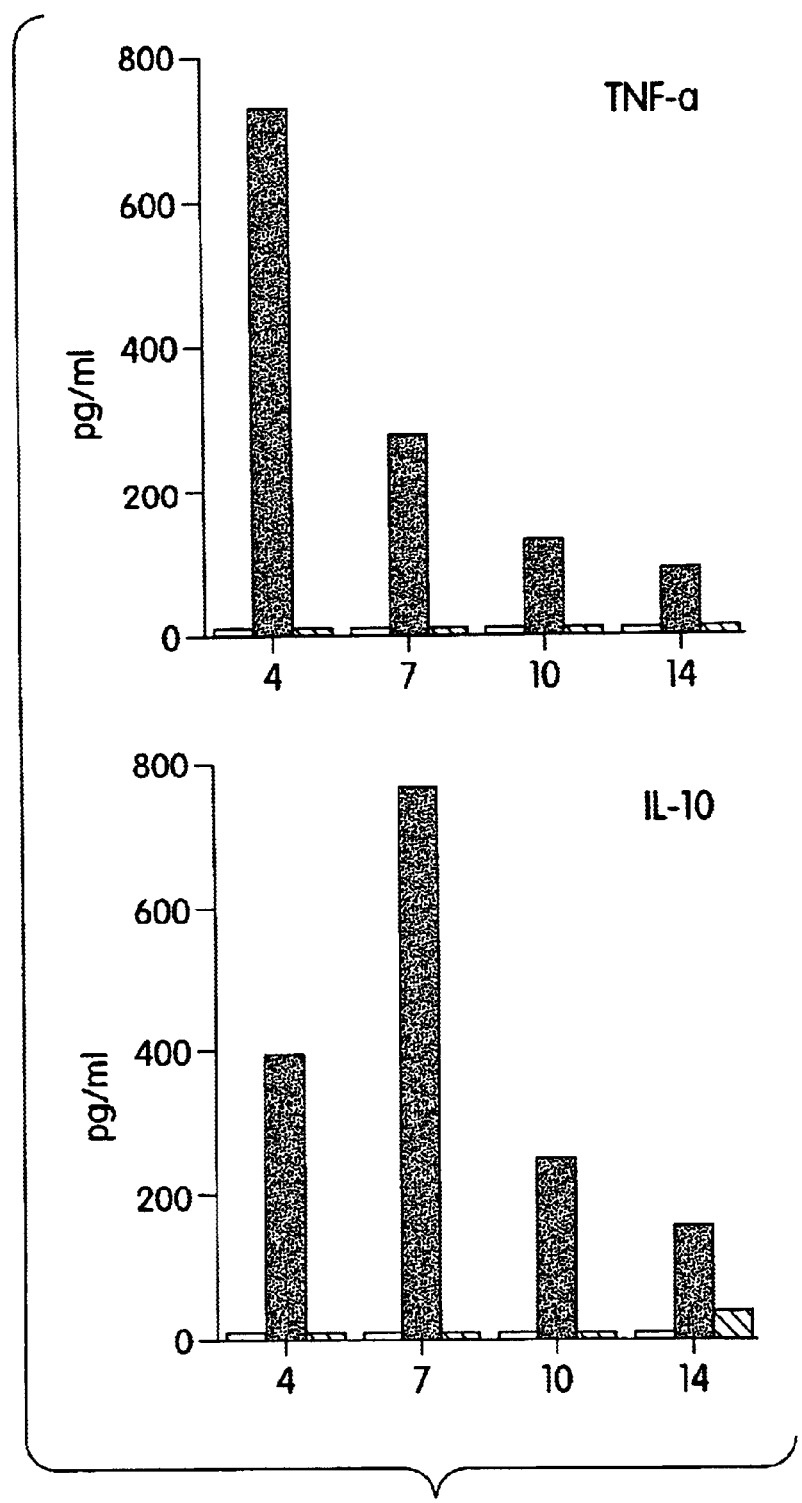

FIGS. 4A–C. Inhibition of HIV-1 Replication by Non-pyrogenic Forms of LPS. FIG. 4A is representative of 4 different experiments and demonstrates that MLK986/37 inhibits HIV-1 chemokines. FIG. 4B MLK986/37 induced HIV-1 inhibition in MDM is reversed by addition of a mixture of neutralizing antibodies against RANTES, MIP-1α, and MIP-1β (from R&D Systems Inc.; 200 ug/ml each). FIG. 4C HIV-1 replication inhibition occurred without inducing pyrogenic cytokines. Figure Legend:

■Control

□LPS

▨LPS mutant

Figure 5:
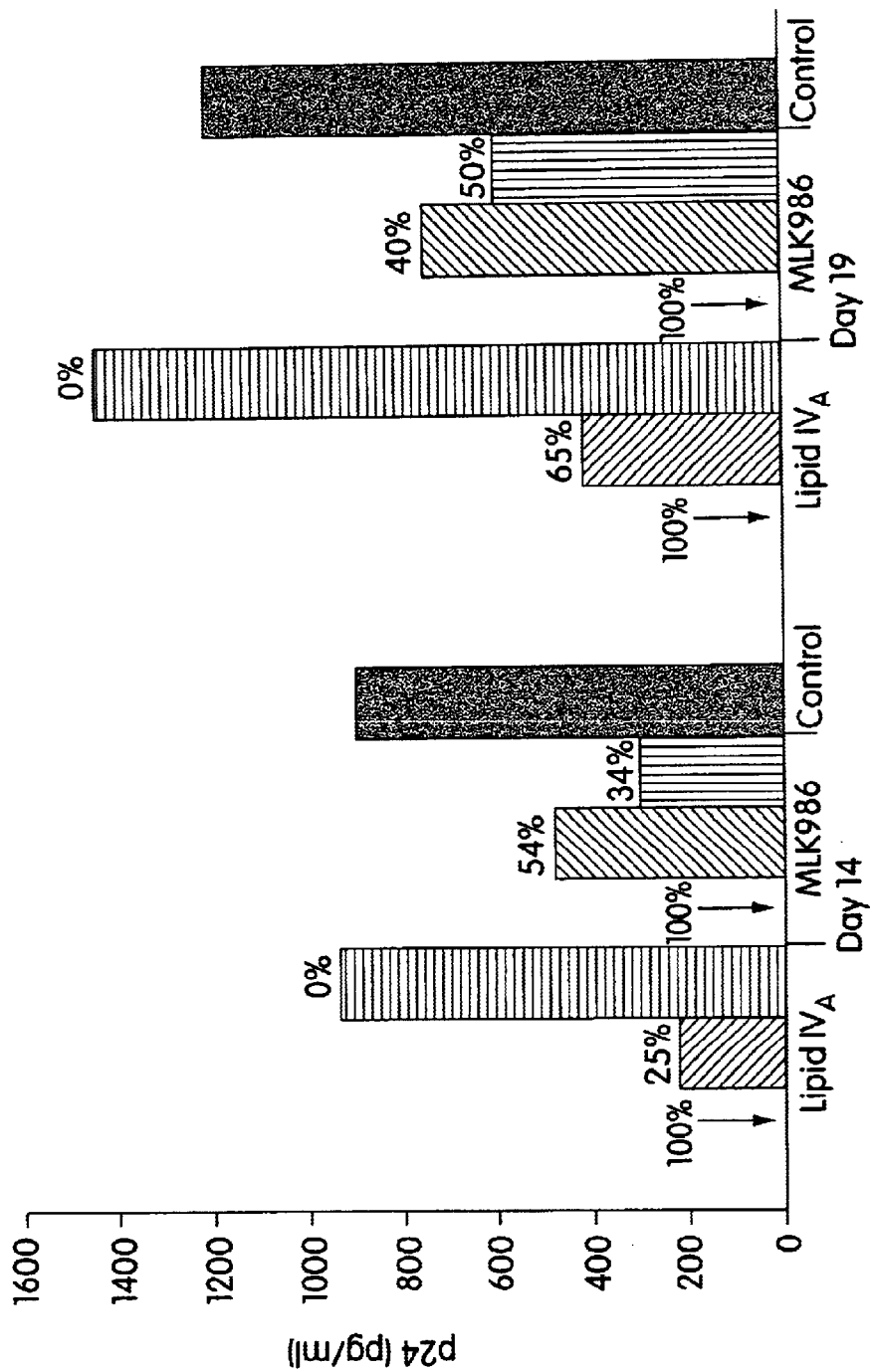

FIG. 5. Lipid A antagonist, lipid $IV_A$, inhibits HIV replication. PBMCs were treated with synthetic lipid $IV_A$ at 1000 ng/ml, 100 ng/ml and 10 ng/ml for 24 hours. The treated cells were subsequently infected with 0.200 ng of HIV-$1_{BAL}$ (Cocchi et al, supra) for 2 hours, washed twice and incubated for a further 19 days. Culture supernatants were then collected and the level of p24 in these supernatants was measured by ELISA (R&D Systems). The results of this assay show that lipid $IV_A$ suppresses the replication of HIV-$1_{BAL}$ in a dose-dependent manner. Figure Legend:

□Lipid IVa (1000 ng/ml)

▨Lipid IVa (100 ng/ml)

▤Lipid IVa (10 ng/ml)

□MLK986/42 (1000 ng/ml)

▨MLK986/42 (100ng/ml)

▤MLK986/42 (10 ng/ml)

5. DETAILED DESCRIPTION OF THE INVENTION

The present invention relates to forms of lipid A and LPS which have reduced pyrogenicity as exhibited by reduced proinflammatory and endotoxic activity, relative to wild-type lipid A and LPS respectively, yet stimulate secretion of β-chemokines and are effective at inhibiting HIV replication and/or infection in vitro or in vivo, decreasing viral load, and/or treating or preventing disorders associated with HIV infection. The present invention also relates to LPS and lipid A antagonists which have reduced proinflammatory activity, yet stimulate secretion of β-chemokines and are effective at inhibiting HIV replication and/or infection in vitro or in vivo, decreasing viral load, and/or treating or preventing disorders associated with HIV infection. The LPS and lipid A analogs (including antagonists) of the present invention preferably induce the secretion of β-chemokines but exhibit decreased induction relative to wild-type LPS and lipid A of the secretion of proinflammatory cytokines, such as, IL-β, IL-6 and TNF-α, thereby providing a non-toxic treatment of immunodeficiency virus infection, in particular, HIV infection and its sequelae, ARC and AIDS. The LPS and lipid A variants, derivatives, and analogs of the present invention exhibit decreased pyrogenicity i.e., preferably induce the secretion of β chemokines but exhibit substantial induction relative to wild-type LPS and lipid A of proinflammatory cytokines. Non-pyrogenic derivatives of lipid A and LPS can be identified by their failure to elicit a toxic or endotoxic response in mammals, their lack of proinflammatory activity and/or their lack of induction of secretion of significant levels of pyrogenic cytokines, e.g., IL-7B, IL-6, TNFα. Preferably, non-pyrogenic derivatives are used in the therapeutic methods and compositions of the invention; alternatively, derivatives of reduced pyrogenicity relative to wild-type LPS or lipid A may be employed. LPS antagonists and lipid A antagonists can be identified by their ability to interfere or compete with the activities of LPS or lipid A, e.g., to competitively inhibit the interaction between LPS and the cellular receptor for LPS. Thus, by way of example, such an antagonist may be identified by its ability to reduce the physiological manifestation of LPS or lipid A activity, e.g., its ability to reduce TNFα secretion from LPS-stimulated PBMCs.

Efficacy in treating or preventing HIV infection may be demonstrated by detecting the ability to inhibit the replication of the HIV virus, to inhibit HIV transmission, or to prevent HIV from establishing itself in its host, or to prevent, ameliorate or alleviate the symptoms of a disease caused by HIV infection, or prevent disease progression. The treatment is considered therapeutic if there is, for example, a reduction in viral load, decrease in mortality and/or morbidity.

In specific embodiments, the invention provides an LPS variant with substantially reduced pyrogenicity isolated from gram negative organisms containing at least one mutation selected from the group kdsA, kdsB, htrB or msbB. The present invention further provides an isolated preparation of LPS which has been modified relative to wild-type to yield its reduced or non-pyrogenic properties, including but not limited to the group of monophosphoryl lipid A, penta-acyl lipid A, lipid $IV_A$ or lipid X. The present invention further provides for analogs or derivatives of lipid A or lipopolysaccharide achieved by deacylation, by the treatment with acyloxyacyl hydroxylase or by the treatment with an alkali. The present invention further provides synthetic LPS and lipid A molecules which substantially lack or exhibit reduced proinflammatory activity and are effective at inhibiting HIV replication.

The present invention further relates to therapeutic methods and compositions for treatment and prevention of disorders associated with immunodeficiency virus infection based on non-pyrogenic or reduced-pyrogenic LPS and lipid A preparations and therapeutically effective analogs and derivatives thereof. The invention provides for treatment of HIV infection by administration of a therapeutic compound of the invention. The therapeutic compounds of the invention include preparations of reduced or substantially absent pyrogenicity of LPS and lipid A which do induce β chemokines, such as MIP-1α and MIP-1β, and related derivatives and analogs thereof. Lipopolysaccharides and lipid A variants, analogs and derivatives which are effective for treatment and prevention of HIV infection can be identified by in vitro and in vivo assays such as those described in Section 5.3 infra.

In a preferred embodiment, a therapeutic composition of the invention comprises an isolated lipopolysaccharide isolated from gram negative organisms containing at least one mutation from the group kdsA, kdsB, htrB or msbB, or a synthetic analog of lipopolysaccharide which has been modified relative to wild-type to yield reduced or absent pyrogenic properties, including but not limited to the group of monophosphoryl lipid A, penta-acyl lipid A, lipid IV$_A$ or lipid X. In other preferred embodiments, the therapeutic comprises a lipopolysaccharide analogue or derivative achieved by deacylation, by treatment with acyloxyacyl hydroxylase or by treatment with an alkali. In yet another preferred embodiment, the therapeutic comprises synthetic LPS and lipid A molecules which lack or exhibit reduced proinflammatory activity and are effective at inhibiting HIV replication.

For clarity of disclosure, and not by way of limitation, the detailed description of the invention is divided into the subsections with follow.

5.1. Lipopolysacchride Variants and Derivatives and Analogs Thereof with Reduced or Absent Pyrogenicity The invention provides isolated preparations of non-pyrogenic or reduced pyrogenic variants of LPS and lipid A and isolated preparations of LPS or lipid A antagonists which exhibit decreased induction relative to wild-type LPS and lipid A of proinflammatory activity, yet preferably stimulate secretion of β chemokines and are effective for treatment or prevention of immunodeficiency virus and/or HIV infection and resulting disorders. Pyrogenicity of the preparations may be determined by measuring the ability of the LPS or lipid A preparation to stimulate the secretion of proinflammatory cytokines, e.g., IL-β, IL-6 and TNFα, or by any method known in the art. Effectiveness of the lipopolysaccharides of the invention for treatment or prevention of HIV infection can be determined by any of the methods disclosed in Section 5.3 infra or by any method known in the art. In a specific embodiment, the LPS and lipid A preparations and derivatives or analogs thereof inhibit HIV infection.

In a preferred embodiment the lipid A antagonists or lipopolysaccharides are derived from gram negative microorganisms that have mutations in one of the following genes: kdsA, kdsB, htrB or msbB.

In a preferred embodiment of the present invention, lipid X or lipid IV$_A$, both LPS and lipid A antagonists of reduced or absent pyrogenicity, are used for the treatment of HIV. Lipid X is a monosaccharide precursor of lipid A (Rietschel et al., supra; and Raetz, supra (1993) and lipid IV$_A$, a tetra-acyl precursor of lipid A (Wang et al., Infect Immun, 59(12):4655–4664. (1991); Ulmer et al., Infect Immun., 60(12):145–5152 (1992); Kovach et al., J. Exp. Med., 172:77–84 (1990) and Rietschel et al., supra). These molecules are of interest because both lipid X and lipid IV$_A$ display non-pyrogenic characteristics in vitro (Golenbock et al., Infect. Immun., 56:779 (1988); Golenbock et al., J. Biol. Chem., 266:19490 (1991); Wang et al., Infect. Immun., 59(12); 4655–4664 (1991); Ulmer et al., Infect Immun., 60(12):145–5152 (1992); Kovach et al., J. Exp. Med., 172:77–84 (1990); Rietschel et al., supra; and Raetz, supra). In addition, lipid X and lipid IV$_A$ are LPS and lipid A antagonists (Wang et al., supra; Ulmer et al., supra; Kovach et al., supra; Rietschel et al., supra; and Raetz, supra). The activity of these molecules differs, since lipid X is non-pyrogenic in mice, whereas lipid IV$_A$ displays similar toxicity of that of lipid A in mice (Golenbock et al., supra (1988); Golenbock et al., supra (1991)). Furthermore, CD14 has been shown to enhance the cellular responses to LPS and lipid IV$_A$ in mice without imparting ligand-specific recognition (Delude et al., Proc. Natl. Acad. Sci., 92:9288 (1995)). Together, these results suggested that individual LPS antagonists may operate through distinct mechanisms.

In yet another preferred embodiment of the present invention, forms of LPS of reduced or absent pyrogenicity isolated from mutant strains of gram negative bacteria may be used in accordance with the present invention to treat HIV. There is growing evidence that mutations in htrb and msbB may influence the biosynthesis of lipid A. These mutants are temperature sensitive and LPS isolated from these mutants stains less intensely on silver-stain gels (Karow et al., J. Bacteriol, 173:741–750 (1991); Karow and Georgopoulos, J. Bacteriol 174:702–710 (1992)). Although the basis for the temperature-sensitive growth phenotype of the htrb and msbB mutants has remained cryptic, there has been speculation that these mutants produce defective lipid A precursors (Karow and Georgopoulos, supra). This assumption was based on altered membrane lipid content (Karow et al., J. Bacteriol., 174:7407 (1992)). E. coli mutants carrying mutations in htrb, msbB or both htrb and msbB produce non-pyrogenic LPS when grown at temperatures above 33° C. and below 44° C. (PCT International Publication No. WO 97/18837 dated May 29, 1997). This non-pyrogenic LPS from E. coli mutants carrying mutations in htrb, msbB or both htrB and msbB also displays LPS antagonist activity (PCT International Publication No. WO 97/18837). Recent evidence demonstrated that HtrB and MsbB function as myristoyl and lauroyl transferases, respectively and are necessary for the synthesis of complete lipid A (Clementz et al., J. Biol. Chem., 271:12095 (1996); Summerville et al., J. Clin. Invest., 97:359 (1996). Collectively, these data suggest that the non-pyrogenic or reduced-pyrogenic property of LPS isolated from E. coli strains carrying mutations in htrB, msbB or both htrB and msbB when grown at temperatures above 33° C. and below 44° C. is the result of an accumulation of lipid A precursors, such as lipid IV$_A$ (in htrB, mutants) and penta-acyl lipid A (in the single msbB mutant).

Thus, several mutants of E. coli with defective lipid A biosynthesis have been shown to accumulate LPS and lipid A analogs with LPS antagonist activity and LPS analogs isolated from these strains may be used in accordance with the present invention to treat or prevent HIV infections and disorders associated therewith.

In another embodiment of the present invention, LPS antagonists to be used in accordance with the present invention may be produced by deacylation of LPS or lipid A. LPS antagonists may be developed using chemical (Neter et al., J. Immunol., 76:377 (1956); Qureshi et al., J. Biol. Chem., 266:6532 (1991)) or enzymatic (Munford and Hall, J. Biol. Chem., 264:15613 (1989); Erwin and Munford, J. Biol. Chem., 256:16444 (1990)) procedures known to those of ordinary skill in the art. Chemical production of LPS antagonists from LPS or lipid A can be accomplished by alkaline hydrolysis of LPS or lipid A (Neter et al., supra; Qureshi et al., supra). Enzymatic production of LPS antagonists from LPS or lipid A can be accomplished by treating LPS or lipid A with acyloxyacyl hydrolase. A source of acyloxyacl hydrolase are professional phagocytes which normally produce this enzyme to be utilized by the host to detoxify LPS (Munford and Hall, supra; Erwin and Munford, supra).

In another embodiment, LPS and lipid A compositions of reduced or absent pyrogenicity which may be used in accordance with the present invention may be isolated from bacteria such as *Rhodobacter sphaeroides* that have LPS with reduced pyrogenicity. Not all gram negative bacteria produce LPS structures that display endotoxin activity (Salimath et al., Qureshi et al., J. Biol. Chem., 266:6532 (1991); Qureshi et al., J. Biol. Chem., 263:5502 (1988)). LPS structures which have significantly less pyrogenicity than LPS isolated from *E. coli*, e.g., if the LPS structure stimulates significantly less or no secretion of IL-1β, IL-6 or TNFα from peripheral blood monocytes (PBMCs), the LPS structure may be used in accordance with the present invention. For example, but not by way of limitation, *Rhodobacter sphaeroides* LPS has an unusual pentaacyl structure that is significantly less pyrogenic that *E. coli* LPS in vitro and in vivo (Salimath et al., Eur. J. Biochem., 136:195 (1983); Qureshi et al., J. Biol. Chem., 266:6532 (1991). Monophosphoryl or diphosphoryl RSLA can also be used in accordance with the present invention. Moreover, *R. sphaeroides* lipid A (RSLA) is an effective LPS antagonist (Salimath et al., Eur. J. Biochem., 136:195 (1983); Qureshi et al., J. Biol. Chem., 266:6532 (1991); Qureshi et al., J. Biol. Chem., 263:5502 (1988)) and prevents LPS induced lethality in mice (Salimath et al., Eur. J. Biochem., 136:195 (1983); Qureshi et al., J. Biol. Chem., 266:6532 (1991); Qureshi et al., J. Biol. Chem., 263:5502 (1988)). In a further embodiment of the present invention, monophosphoryl RSLA may be a more effective LPS antagonist than diphosphoryl RSLA and therefore is used in accordance with an embodiment of the present invention for the treatment of HIV (Salimath et al., Eur. J. Biochem., 136:195 (1983); Qureshi et al., J. Biol. Chem., 266:6532 (1991); Qureshi et al., Qureshi et al., J. Biol. Chem., 263:5502 (1988)).

In accordance with the present invention, lipopolysacchrides and lipid A analogs of reduced or absent pyrogenicity may be yielded by the modification of naturally occurring lipopolysaccharides. Such modification can include, but are not limited to treating the lipopolysaccharide or lipid A with acyloxyacyl hydrolase, or by a alkaline hydrolysis process or a deacylation process.

In yet a further embodiment of the present invention, synthetic LPS antagonists may be used in accordance with the present invention for the treatment of HIV. For example, but not by way of limitation, synthetic lipid A and lipid X analogs (Ulmer et al., Infect. Immun, 60:5145 (1992); Perera et al., Infect Immun., 61:2015 (1993); Wang et al., Infect. Immun., 59:4655 (1991); Kotani et al., Infect. Immuno., 54:673 (1986): Kotani et al., Infect Immun., 49:225 (1985); Fagan et al., J. Immunol., 153:5230 (1994)) can be used. Disaccharide LPS antagonists, which resemble lipid IV$_A$, may also be used in accordance with the present invention (Ulmer et al., supra; Perera et al., supra); Wang et al., supra; Kotani et al., supra (1985); Kotani et al., supra (1986)). A second group of synthetic molecules were designed to be analogs of *R. sphaeroides* lipid A and are potent LPS antagonists (Christ et al., Science 269:80 (1995); Christ et al., J. Am. Chem. Soc., 116:3637 (1994)) and can be used in accordance with the present invention. A further set of synthetic LPS antagonists have been described that are composed of monosaccharide backbones and more closely resemble lipid X; these can be used in accordance with the present invention (Perera et al., supra). Collectively, these molecules have proven to display potent LPS antagonist activity in vitro (Ulmer et al., supra; Perera et al., supra); Wang et al., supra; Kotani et al., supra (1985); Kotani et al., supra (1986)) and have been evaluated for safety in humans (Bunnell et al., Crit. Care Med. Suppl., 23:147 (1995); Bunnell et al., Crit. Care Med. Suppl., 23: A151 (1995)). In a preferred embodiment, synthetic analogs of LPS can be generated which contain a 2-deoxy-2-aminogluconate residue in place of the glucosamine-1-phosphate at the reducing end and further bear a galacturonic acid moiety instead of a phosphate at position 4'.

In another embodiment of the present invention, the lipopolysaccharides and lipid A molecules and analogs and derivatives thereof can be modified in accordance with the present invention so that they are shortened or condensed, e.g., the carbon backbone may be shortened to a 5 carbon backbone. Further, the LPS and lipid A structures of the present invention may be modified so that one or more or all of the glucosamine residues are substituted with galactosamine residues. The diphosphoryl LPS and lipid A structures of the present invention can be converted to either nonphosphoryl or monophosphoryl LPS and lipid A structures in accordance with the present invention. The lipid A and LPS structures of the present invention can be modified to have more or less charge, e.g., the lipid A or LPS structures can be modified to be more charged by the addition of amine groups. The lipid A and LPS structures can further be modified so that they are less immunogenic, i.e., less recognized by the immune system of the host. In accordance with the present invention, any modification of the LPS and lipid A structures of the present invention which results in a non-pyrogenic or reduced-pyrogenic analog or derivative, i.e., analogs which exhibit decreased induction relative to wild-type LPS and lipid A of proinflammatory activity yet stimulate secretion of β chemokines and are effective for treatment or prevention of HIV infection can be used. The invention thus also provides a method of screening LPS and -lipid A derivatives and analogs for anti-immunodeficiency virus activity, e.g., by assaying them for the ability to inhibit immunodeficiency virus replication or expression of immunodeficiency virus RNA or protein or to alleviate symptoms of an immunodeficiency virus-induced disorder.

In another embodiment of the present invention, a mixture of one lipid A or LPS or analog or derivative of the present invention mixed with at least one other LPS or lipid A structure or analog or derivative thereof of the present invention can be used to treat or prevent HIV infections and disorders associated therewith. In accordance with a specific embodiment of the present invention, a mixture comprising at least one LPS antagonist with an LPS or lipid A structure isolated from a gram negative organism, wherein the LPS antagonist is in molar excess of the LPS or lipid A structure can be used to treat or prevent HIV infection and disorders associated therewith.

The lipopolysaccharides and lipid A molecules and analogs and derivatives thereof of the present invention may be associated or conjugated with other molecules. These molecules may be macromolecular carrier groups including, but not limited to, lipid-fatty acid conjugates, polyethylene glycol, protein or carbohydrate. The associated or conjugated molecule may also provide bifunctionality to the lipopolysaccharide by, for example, targeting the lipopolysaccharide to a predetermined tissue or cell type, such as T lymphocytes. The association or conjugation between the lipopolysaccharide and the other molecule may be the result of a direct interaction, such as for example, through a chemical bond or ionic interaction, or alternatively, the association or conjugation with the other molecule may be through a linking group. The linking group may be known in the art which serves to link the lipopolysaccharide, or pharmaceutically acceptable derivative thereof, with the other molecule. Suitable linking groups include saccharides, oligosaccharides, peptides, proteins, $C_2$–$C_{20}$ alkyl, oxyalkylene chains or any other group which does not inhibit the ability of the lipopolysaccharide of the composition to inhibit HIV replication. The ability of the lipopolysaccharide components of the composition to inhibit HIV replication may be determined by applying assays described in Section 5.3.

The lipopolysaccharides or pharmaceutically acceptable derivatives of the present invention may be monosaccharide precursors of lipid A, such as lipid X, or may be a tetra-acyl precursor of lipid A, such as lipid $IV_A$, etc. Competitive inhibition is typically enhanced by increased valence, as once the first contact is made, the probability of subsequent contact taking place is favored thermo-dynamically. The use of multivalents is especially useful in blocking low affinity events where high avidity can compensate. Such may be the case for the lipid A antagonists of the present invention which are thought to function by competitively inhibiting LPS from interacting with CD14. In a specific embodiment, the composition comprises multivalent monosaccharide precursors of lipid A in order to increase the potency and/or biological half life of the pharmaceutical. In one embodiment, lipid X is found in multiple copies on a compound for use in the invention.

Multivalent carbohydrates can be prepared using methods known in the art to prepare a branching complex carbohydrate, which conceptually resembles a tree in which each branch contains a lipid A precursor, such as, lipid X. Alternatively, monovalent carbohydrates can be associated covalently or noncovalently with a polymer using techniques known in the art (see e.g., Langer et al., International Patent Publication No. WO94/03184, published Feb. 17, 1994, which is herein incorporated by reference in its entirety). The oligosaccharide units of the lipopolysaccharides of the present invention can be bound directly or through a linking group to the polymer using known techniques so as to produce a conjugate in which more than one individual molecule of the oligosaccharide of each lipopolysaccharide is covalently attached. Suitable linking groups include, but are not limited to saccharides, oligosaccharides, peptides, proteins, $C_{2-20}$ alkyl, oxalkylene chains or any other group which does not prevent the lipopolysaccharide from inhibiting HIV replication. Suitable polymers are known in the art and include, but are not limited to, a polyol, a polysaccharide, avidin, lipids, lipid emulsions, liposomes, a dendrimer, human serum albumin, a protein, polylysine, dextran, a glycosaminoglycan, cytclodextrin, agarose, sepharose, and polyacrylamide.

The lipopolysaccharides or pharmaceutically acceptable derivatives of the invention may be associated (e.g., ionic interaction) or conjugated (e.g., covalent linkage) with a ligand for a cell-surface molecule so as to target the lipopolysaccharides to tissue or cells expressing these molecules. Such oligosaccharide-ligand combinations may be through direct interaction of the oligosaccharide and ligand or indirectly using linker means known in the art. The oligosaccharide/ligand combination may be generated by techniques known in the art (See e.g., Stowell & Lee, 1980, Advances in Carbohydrate Chemistry, 37:225–281) and are generated so as not to inhibit the ability of the lipopolysaccharide to inhibit HIV infection. The ability of the lipopolysaccharide/ligand combination to inhibit HIV replication may routinely be determined applying in vitro assays described in Section 5.3 herein and known in the art. The ability of the lipopolysaccharide/ligand combination to bind to the cell-surface binding partner of the ligand may be determined using techniques known in the art. The ligand component of the lipopolysaccharide ligand combination may comprise monoclonal antibody, cell-surface receptor ligand or other homing molecules for therapeutically significant targets that are known or may routinely be identified and isolated and/or generated using techniques known in the art. Ligands encompassed by this embodiment include, but are not limited to, CD4-derived peptide bound by gp120of HIV (from the D1 domain of CD4 and distinct from the MHC-binding region (see e.g., Sakihama et al., 1995, PNAS 92:644–648; Ryu et al., 1994, Structure 2:59–74), peptides derived from the extracellular domain of chemokine receptors (e.g., CC-CXR-5 or fusion) to which the V3 loop of gp120binds (Choe et al., 1996, Cell 85:1135–1148; Feng et al., 1996, Science 272:872–30 876).

5.2. Synthesis and Isolation of Lipopoltsaccharides

In accordance with the present invention the lipopolysaccharides, LPS analogs (e.g., antagonists), and lipid A analogs (e.g., antagonists) of the present invention can be purified from gram negative microorganisms or produced using classical organic chemistry synthetic techniques known in the art. Lipid A and LPS antagonists can be identified by their ability to interfere or compete with the activities of LPS or lipid A, e.g., to competitively inhibit the interaction between LPS and the cellular receptor for LPS, for example, as reflected by the inhibition of a biological consequence of such an interaction. Alternatively, in another embodiment, the lipopolysaccharide analogs and derivatives of the present invention may be prepared by enzymatic processes. Some non-pyrogenic forms of LPS and lipid A are commercially available (e.g., from ICN).

5.2.1 Purification of Lipopolysaccharides from Microorganisms 5.2.1.1 Sources of Lipopolysaccharides Native preparations of non-pyrogenic or reduced-pyrogenic forms of lipid A and LPS amy be obtained from a variety of sources. In accordance with the present invention, a variety of gram negative strains may be used as the starting material in producing non-pyrogenic or reduced-pyrogenic forms of LPS and lipid A. Examples of these strains include, but are not limited to, *Haemophilus influenzae, Escherichia coli, Salmonella enterica, Klebsiella pneumoniae, Bordella pertussis, Pseudomonas aeruginosa, Chlamydia psittaci, Rhodobacter spearoides*, it and *Legionella pneumophila*.

In accordance with the present invention, the non-pyrogenic or reduced-pyrogenic LPS and lipid A preparations may be isolated from gram negative strains carrying mutations in one of the following genes: kdsA, kdsB, htrB, msbB or both htrB and msbB. The genetics of lipid A biosynthesis are well described (Raetz, supra; Raetz, Ann. Rev. Biochem 59:129–170 (1990); and Schnaitman and Klena, supra). The majority of mutations that prevent the biosynthesis of lipid A, such as mutations in 1pxA, 1pxB, kdsA, kdsB, kdtA, are lethal as the biosynthesis of lipid A is essential for cell survival (Rick et al., J. Biol. Chem., 252:4904–4912 (1977); Rick and Osborn, J. Biol. Chem., 252:4895–4903 (1977); Raetz et al., J. Biol. Chem., 260:16080–16088 (1985); Raetz, supra (1990); Raetz, supra (1993); and Belunis et al., J. Biol. Chem., 270:27646 (1995)). For the most part, therefore, analysis of these genes has involved the use of temperature-sensitive mutants, which only display null phenotypes under non-permissive conditions (Rich et al., supra; Rich and Osborn, supra; Raetz et al., supra; Raetz, supra (1990); Raetz, supra (19930; and Belunis et al., supra). When grown under non-permissive conditions, 1pxB, kdsA, kdsB, kdsA mutants accumulate non-pyrogenic precursor forms of LPS (to about 50% of the total LPS), such as lipid X (also called 2,3-diacyl-glucosamine-1-phosphate) or lipid IV$_A$ (Raetz et al., supra; Belunis et al., supra).

Alternatively, non-pyrogenic or reduced-pyrogenic LPS and lipid A preparations may be isolated from gram negative microorganisms carrying at least one mutation in the genes encoding for myristoyl transferase or lauroyl transferase. Gram negative microorganisms carrying mutations in the pgsA gene, which encodes phosphatidylglycerophospate synthase; 1pxB, the structural gene for disaccharide synthase; the 1pxA gene, encoding UDP-GlcNAc O-acetyltransferase; kdtA the structural gene encoding the KDO (3-deoxy-D-manno-actulosonic acid) transferase, may also be used as a source of non-pyrogenic or reduced-pyrogenic LPS or lipid A structures in accordance with the present invention.

In a preferred embodiment of the present invention, non-pyrogenic forms of LPS may be isolated from strains of E.coli carrying mutations in both htrB and msbB, which produce non-pyrogenic LPS when grown at temperatures above 33° C. and below 44° C. (See PCT International Publication No. WO 97/18837). In a preferred embodiment of the present invention, non-pyrogenic LPS is isolated from the E. coli htrB1::Tn10 msbB::Ωcam double mutant MLK986. In yet another preferred embodiment, non-pyrogenic preparations of lipid A are isolated from gram negative bacteria KDO-deficient mutants which accumulate lipid IV$_A$, a non-pyrogenic form of lipid A (Goldman et al., 1988, J. Bacteriol. 170:2185–2192; Raetz et al., 1985, J. Biol. Chem. 260:16080–16088).

Many of the proteins involved in lipid A metabolism are essential to bacteria vitality and therefore mutations in these genes must be introduced as ones inducible by growth conditions, i.e., temperature sensitive mutants, or the mutant genes may be under the control of an inducible promoter, such as a tetracycline promoter, tetR, or a repressible promoter, such as a lexA-repressed promoter. Mutations may be introduced into the genomes of gram negative bacteria using standard recombinant DNA techniques well known to those of ordinary skill in the art. Mutations in the designated genes listed above may consist of the deletion of the gene or a portion thereof, insertion of nucleic acids into the gene coding region, missense mutations, nonsense mutations (see, e.g., Miller 1992, A Short Course in Bacterial Genetics, Cold Spring Harbor Press; Sambrook et al., 1989, Molecular Cloning, A Laboratory Manual, Cold Spring Harbor Laboratory, 2d Ed., Cold Spring Harbor, N.Y., Glover), etc. Any technique for mutagenesis known in the art may be used, including but not limited to, chemical mutagenesis, in vitro site-directed mutagenesis (Hutchinson, C. et al., 1978, J. Biol. Chem. 253:6551), use of TAB™ linkers (Pharmacia), PCR with mutant primers, etc.

Further, in vivo cloning techniques can be used to introduce mutation-containing nucleic acids into the genomes of gram negative bacteria (see, e.g., Miller 1992, A Short Course in Bacterial Genetics, Cold Spring Harbor Press; Sambrook et al., 1989, Molecular Cloning, A Laboratory Manual, Cold Spring Harbor Laboratory, 2d Ed., Cold Spring Harbor, N.Y., Glover), etc.

Other bacterial strains may be used in accordance with the present invention as a source of forms of LPS and lipid A of reduced or absent pyrogenicity. For example, Rhodobacter sphaeroides LPS has an unusual pentaacyl structure that is significantly less pyrogenic than E. coli LPS in vitro and in vivo (Salimath et al. supra; Qureshi et al. supra, 1991; Qureshi et al. supra 1988). R. sphaeroides lipid A (RSLA) is an effective LPS antagonist (Salimath et al. supra) and prevents LPS induced lethality in mice. Bacterial strain Rhizobium leguminosarum may also be used as a source of non-pyrogenic form of LPS and lipid A, in accordance with the present invention. Lipid A isolated from R. leguminosarum lacks phosphate altogether and does not contain a glucosamine disaccharide (Bhat et al. 1992 Glycobiology 2:535–539) and is a very potent antagonist of lipid A. R. leguminosarum lipid A contains a 2-deoxy-2-aminogluconate residue in place of the glucosamine 1-phosphate at the reducing end, and bears a glacturonic acid moiety instead of a monophosphate at position 4'.

5.2.1.2 Isolation of Lipopolysaccharides

The lipopolysaccharides of the present invention may be purified from gram negative microorganisms using any technique known in the art. In this embodiment, the lipopolysaccharides of the present invention are isolated from the cell wall of the bacteria. In gram-negative bacteria, the cell wall is far more complex than for gram positives and contains glycopeptide, lipopolysaccharide, phospholipid and protein. Up to 20% of the wall content may be lipids but only a proportion of these are readily extractable by conventional solvent methods. That is due to the covalent nature of the lipopolysaccharide linkages. In spite of the foregoing, in accordance with the present invention, the lipopolysaccharides of the present invention may be isolated from gram-negative bacteria using the procedures described infra.

By way of example, and not by limitation, the lipopolysaccharides of the present invention may be isolated by the following method:

Bacterial strains are cultured on solid media both at 30° C., 37° C. or 42° C. prior to seeding the liquid media. Liquid cultures (1L) are seeded the following day at a starting inoculum of ca. $1 \times 10^4$ cfu/ml and grown for 16 hr at 30° C., 37° C. or 42° C. with shaking (250 opm).

The liquid cultures are harvested by centrifugation at 7000×g for 10 min, washed once in 250 ml endotoxin-free irrigation saline (Baxter) and the weight of the bacterial pellets was determined. The pellets then are resuspended in endotoxin-free water (Baxter) at a final density of 2% w/v±0.25%. Subsequently, LPS is isolated by two cycles of hot-water phenol extraction. In short, the bacterial suspensions are heated to 70° C. to which an equal volume of pre-warmed phenol is added and mixed for 15 min at 70° C. The mixtures are cooled to 25° C. and then centrifuged at 18,000×g for 15 min. Following this centrifugation the aqueous phases are removed, placed into dialysis tubing (SpectraPor) and dialyzed against running distilled H$_2$O overnight. The retentates are then placed into fresh 50 ml polypropylene tubes and treated with RNaseA (100 μg/ml) at 37° C. for 1 hr, followed by DNaseI (50 μg/ml and 5 mM Mgcl$_2$) at 37° C. for 1 hr, followed by Pronase (250 μg/ml) at 37° C. for 1 hr. Then EDTA is added to a final concentration of 5 mM and the hot-water phenol extraction procedure described above is repeated. Following dialysis the retentates are centrifuged at 20,000×g for 15 min at 4° C. The supernatants are transferred to fresh Beckman 50Ti tubes and the LPS is pelleted by centrifugation at 110,000×g for 2H at 4° C. The supernatants are discarded and the pellets are vacuum dried. Each LPS preparation is evaluated for DNA and protein contamination by standard techniques in the art, such as SDS-PAGE and silver stain, BCA protein estimate assay and UV spectrophotometry.

Also included within the scope of the present invention are LPS and lipid A molecules which are differentially modified during or after synthesis to yield reduced or absent pyrogenic properties of the preparation. In specific embodiments, the LPS and lipid A molecules are treated by alkaline hydrolysis or acyloxyacyl hydrolase. Any of numerous chemical modifications may be carried out by known techniques, such as acylation, deacylation, formylation, oxidation, reduction, etc.

5.2.2 Synthesis of Lipopolysaccharides

Potent synthetic lipid A molecules with strong LPS antagonist properties and of reduced or absent pyrogenicity may be synthesized by a variety of organic chemistry synthetic techniques. In one embodiment of the present invention, the synthetic lipid A and LPS molecules are modeled after LPS molecules of reduced or absent pyrogenicity which occur in nature and molecules with strong LPS antagonist activities which occur in nature.

The lipopolysaccharide is a complex polymer in four parts. Outermost is a carbohydrate chain variable length (called the O-antigen) which is attached to a core polysaccharide. The core polysaccharide is divided into the outer core and the backbone. These two structures vary between bacteria. Finally the backbone is attached to a glycolipid called lipid A. The link between lipid A and the rest of the molecule is usually via a number of 3-deoxy-D-mannooctulosonic acid (KDO) molecules. The presence of KDO is often used as a marker for lipopolysaccharide (or outer membrane) even though it is not present in all bacterial lipopolysaccharides. The phosphate and 3-deoxy-D-mannooctulosomic acid (KDO) molecules (the presence of KDO is often used as a marker for lipopolysaccharide) are also substituted. Unsaturated and cyclopropane fatty acids which are common in other lipid types are absent from lipopolysaccharide.

Lipid A is composed of a disaccharide of glucosamines. The amino groups are substituted with 3-hydroxymristate while hydroxyl groups contain saturated (12–16 carbon) acids and 3-myristoxymyristate. Lipopolysaccharides and lipid A may be obtained from commercial sources, e.g., from Sigma. However, by way of example, but not by way of limitation, lipolysaccharides may be synthesized as follows: hydroxy acids and disaccharides are condensed followed by addition of saturated fatty acids. The hydroxy fatty acids may come from acetyl CoA whereas CMP-KDO may serve as the source of the second additional units. After the addition of saturated fatty acids, sugars are added from nucleotide diphosphate derivatives.

The O-antigen is may be synthesized in three stages. For example, but not by way of limitation, the oligosaccharide units are transferred from nucleotide diphosphate carriers to a galactose attached to another lipid carrier. The oligosaccharide units are then polymerized and lipid carriers are released in the process. Finally the complete O-antigen is transferred to the R-core with the release of an isoprenoid carrier.

For an overview of the synthesis of lipopolysaccharides and lipid A structures, see, e.g., Raetz, 1993, *J. Bacteriology* 175:5745–5753. (See also U.S. Pat. Nos. 5,593,969 and 5,191,072).

The polysaccharide unit may also be synthesized with donor saccharide moieties and acceptor moieties which are commercially available and/or may be synthesized through organic synthesis applying techniques known in the art. Activated saccharides generally consist of uridine or guanosine diphosphate and cytidine monophosphate derivatives of the saccharides in which the nucleoside mono and diphosphate serves as a leaving group. Thus, the activated saccharide may be a saccharide-UDP, a saccharide-GDP, or a saccharide-CMP. Nucleoside monophosphates are commercially available, may be prepared from known sources such as digested yeast RNA (see e.g., Leucks et al,. 1979, J. Am. Soc. 101:5829), or routinely prepared using known chemical synthetic techniques (see e.g., Heidlas et al., 1992, Acc, Chem. Res. 25:307; Kochetkov et al., 1973, Adv. Carbohydr. Chem. Biochem. 28:307). These nucleoside monophosphates may then be routinely transformed into nucleoside diphosphates by kinase treatment. For review, see Wong et al., 1994, Enzymes in Synthetic Organic Chemistry, Pergamon Press, Volume 12, pp. 256–264.

Glycosyltransferase enzymes for synthesizing the compositions of the invention can be obtained commercially or may be derived from biological fluids, tissue or cell cultures. Such biological sources include, but are not limited to, pig serum and bovine milk. Glycosyltransferases that catalyze specific glycosidic linkages may routinely be isolated and prepared as described in International Patent Publication No. WO 93/13198 (published Jul. 8, 1993). Alternatively, the glycosyltransferases can be produced through recombinant or synthetic techniques known in the art (For review, see Wong et al., 1994, Enzymes in Synthetic Organic Chemistry, Pergamon Press, Volume 12, pp. 275–279).

The compositions of the invention are preferably synthesized using enzymatic processes (see e.g., U.S. Pat. No. 5,189,674, and International Patent Publication No. 91/16449, published Oct. 31, 1991). Briefly, a glycosyltransferase is contacted with an appropriate activated saccharide and an appropriate acceptor molecule under conditions effective to transfer and covalently bond the saccharide to the acceptor molecule. Conditions of time, temperature, and pH appropriate and optimal for a particular saccharide unit transfer can be determined through routine testing; generally, physiological conditions will be acceptable. Certain co-reagents may also be desirable; for example, it may be more effective to contact the glycosyltransferase with the activated sugar and the acceptor molecule in the presence of a divalent cation. Optionally, an apparatus as described by U.S. Pat. No. 5,288,637, is used to prepare such compositions.

While glycosyltransferases are highly stereospecific and substrate-specific, minor chemical modifications are tolerated on both the donor and acceptor components. Accordingly, the oligosaccharide components of the invention may be synthesized using acceptor and/or donor components that have been modified so as not to interfere with enzymatic formation of the desired glycosidic linkage. The ability of such a modification not to interfere with the desired lycosidic linkage may routinely be determined using techniques and bioassays known in the art, such as, for example, labelling the carbohydrate moiety of the activated sugar donor, contacting the acceptor and donor moieties with the glycosyltransferase specific for forming the glycosidic linkage between the donor and acceptor moieties, and determining whether the label is incorporated into the molecule containing the acceptor moiety.

Also included within the scope of the present invention are LPS and lipid A molecules which are differentially modified during or after synthesis to enhance or yield of reduced or absent pyrogenicity of the preparation. In specific embodiments, the LPS and lipid A molecules are treated by alkaline hydrolysis or acyloxyacyl hydrolase. Any of numerous chemical modifications may be carried out by known techniques, such as acylation, deacylation, formylation, oxidation, reduction, etc.

It is also within the scope of this invention, to synthesize analogs of lipid a having one or more acyloxyacyl groups removed. Lipid A, either chemically synthesized or isolated from a gram negative microorganism may be treated with acyloxyacyl hydrolase in order to achieve or enhance the non-pyrogenic properties of the preparation. Acyloxyacyl hydrolase hydrolyzes the ester bonds between non-hydroxylated fatty acids and the 3-hydroxy functions of 3-hydroxy fatty acids bound in ester or amide linkages to glucosamine disaccharide of lipid A.

It is further within the scope of this invention, to synthesize analogs of lipid A and LPS having one or more non-hydroxylated fatty acids removed. Lipid A or LPS either chemically synthesized or isolated from a gram negative microorganism may be deacylated in order to achieve or enhance the substantially reduced or absent pyrogenicity of the preparation.

5.3 Therapeutic Uses

The invention provides for treatment or prevention of diseases and disorders associated with immunodeficiency virus infection, including, but not limited to, human immunodeficiency virus (HIV), simian immunodeficiency virus (SIV), and feline immunodeficiency virus (FIV), by administration of a therapeutic compound (termed herein "Therapeutic"). Such "Therapeutics" include, but are not limited to: preparations of LPS or lipid A of reduced or absent pyrogenicity, and analogs and derivatives and antagonists thereof, of reduced or absent pyrogenicity. By way of example, but not limitation, the antagonists can be derived from gram negative bacteria, or gram-negative bacteria containing at least one mutation selected from the group consisting of kdsA, kdsB, htrB, msbb and derivative and analogs of the foregoing; LPS orlipid A preparations which have been modified to enhance or yield reduced or absent pyrogenicity, including, but not limited to monophosphoryl lipid A, penta-acyl lipid A, lipid X, lipid $IV_A$ or lipid A or LPS derived from deacylation, treatment with acyloxyacl hydroxylase, or by treatment with an alkaline, and derivatives and analogs of the foregoing; synthetic lipid A and LPS antagonists, such as lipid X, lipid $IV_A$ and prophylactically and therapeutically effective LPS and lipid A analogs and derivatives thereof.

It is also within the scope of this invention, to use therapeutically or prophylactically monosaccharide analogs of lipid A and LPS. Lipid A or LPS structures to be used therapeutically or prophylactically in accordance with the present invention can be either chemically synthesized or isolated from a gram negative microorganism, in which the ester bond of LPS and lipid A is catalyzed or the glycosidic bond of LPS and lipid A is catalyzed resulting in a monosaccharide derivative with enhanced non-pyrogenic properties.

It is also within the scope of this invention, to use mixtures of lipid A or LPS structures and antagonists and analogs and derivatives thereof therapeutically or prophylactically in accordance with the present invention.

In another embodiment of the present invention, a mixture of one lipid A or LPS structure of the present invention mixed with at least one other LPS or lipid A structure of the present invention can be used to treat or prevent immunodeficiency virus infection, including HIV infections and disorders associated therewith. In accordance with the present invention, a mixture comprising at least one LPS antagonist and an LPS or lipid A structure isolated from a gram negative bacteria, wherein the LPS antagonist is in molar excess of the LPS or lipid A structure can be used to treat or prevent HIV infection and disorders associated therein. For example, an LPS or lipid A antagonist combined with a fully active LPS or lipid A, or a monophosphate LPS or lipid A, or a second LPS or lipid A antagonist.

Examples of Therapeutics are those lipopolysaccharides described in Section 5.1 and 5.2.

A preferred embodiment of the invention relates to methods of using a Therapeutic for treatment or prevention of HIV infection, preferably HIV-1 infection, in a human subject. In a specific embodiment, the Therapeutic is used for the treatment or prevention of HIV infection in a human subject who suffers from Kaposi's sarcoma (KS). In the treatment of HIV infection, the Therapeutic of the invention can be used to prevent progression of HIV-1 infection in a seropositive patient to ARC or to AIDS in the patient, or to treat a human patient with ARC or AIDS.

In a preferred aspect of the invention, preparations of reduced or absent pyrogenicity of LPS and/or lipid A and/or derivatives and/or analogs thereof are used to treat HIV infection. The utility of such preparations may be determined by the in vitro and in vivo assays described in Section 5.5 infra or by any other method known in the art.

5.4 Combination Therapy

According to a specific embodiment of the present invention, a preparation of reduced or absent pyrogenicity of LPS or lipid A or an analog or derivative thereof, an inhibitor of HIV viral replication, may optionally be used in combination with other therapeutic agents to enhance the antiviral effect achieved. Preferably a non-pyrogenic preparation of LPS or lipid A or an analog or derivative thereof is used in combination with another antiviral agent. Such additional antiviral agents which may be used with a preparation of reduced or absent pyrogenicity of LPS or lipid A or analog or derivative thereof include but are not limited to those which function on a different target molecule involved in viral replication, e.g., reverse transcriptase inhibitors, viral protease inhibitors, glycosylation inhibitors; those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity.

A preparation of reduced or absent pyrogenicity of LPS or lipid A or an analog or derivative thereof can also be used in combination with retrovirus inhibitors, such as nucleoside derivatives. Nucleoside derivatives are modified forms of purine and pyrimidine nucleosides which are the building blocks of RNA and DNA. Many of the nucleoside derivatives under study as potential anti-HIV medications result in premature termination of viral DNA replication before the entire genome has been transcribed. These derivatives lack 3' substituents that can bind to subsequent nucleosides and result in chain termination. Nucleoside derivatives such as 3' azido-3'-thymidine (AZT) and dideoxyinosine (ddI) have been exploited as inhibitors of HIV-1 replication, both in vitro and in vivo. Nucleoside analogs are currently the only licensed therapeutics for the treatment of HIV infection and AIDS (Fischl et al, 1987 N. Engl. J. Med. 317, 185–191; Mitsuya and Broder, 1987 Nature 325, 773–778). This class of compounds works by inhibiting reverse transcriptase resulting in a block in cDNA synthesis (Mitsuya and Broder, 1987), these inhibitors work early in the infectious cycle of HIV-1 and inhibit integration into T-cell genome. However, AZT therapy leads to development of resistant HIV strains (Larder 1989, 1991, Ibid.) and demonstrates toxicity in AIDS patients upon long-term therapy (Fischl et al., 1987, N. Engl. J. Med. 317:185–191; Creagh-Kirk, et al., 1988, J.A.M.A. 260:3045–3048).

Further, a preparation of reduced or absent pyrogenicity of LPS or lipid A or a derivative or analog thereof can be used in combination with nucleoside derivatives which include but are not limited to, 2',3'-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azido-2',3'-dideoxythymidine (AZT). Alternatively, halogenated nucleoside derivatives may be used, preferably 2',3'-dideoxy-2'-fluoronucleosides including, but not limited to, 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T). Preferably, the 2',3'-dideoxy-2'-fluoronucleosides of the invention are those in which the fluorine linkage is in the beta configuration, including, but not limited to, 2'3'-dideoxy-2'-beta-fluoroadenosine (F-ddA), 2',3'-dideoxy-2'-beta-fluoroinosine (F-ddI), and 2',3'-dideoxy-2'-beta-fluorocytosine (F-ddC). Such combinations allow one to use a lower dose of the nucleoside derivative thus reducing the toxicity associated with that agent, without loss of antiviral activity because of the use of the non-pyrogenic preparation of LPS or lipid A. Moreover, such a combination reduces or avoids viral resistance.

Preferred combinations of preparations of reduced or absent pyrogenicity of LPS or lipid A or derivatives or analogs thereof and nucleoside derivatives within the scope of the present invention include an effective amount of a preparation of reduced or absent pyrogenicity of LPS or lipid A or analogs or derivatives thereof and an effective amount of AZT to treat HIV infection; and an effective amount of a preparation of reduced or absent pyrogenicity of LPS or lipid A or derivative and analogs thereof and an effective amount of ddI.

According to the present invention, preparations of reduced or absent pyrogenicity of LPS or lipid A or derivatives and analogs thereof can also be used in combination with uridine phosphorylase inhibitors, including but not limited to acylouridine compounds, including benzylacyclouridine (BAU); benzyloxybenzylacyclouridine (BBAU); aminomethyl-benzylacyclouridine (AMBAU); aminomethyl-benzyloxybenzylacyclouridine (AMB-BAU); hydroxymethyl-benzylacyclouridine (HMBAU); and hydroxymethyl-benzyloxybenzylacyclouridine (HMBBAU).

According to the present invention, preparations of; reduced or absent pyrogenicity of LPS or lipid A or derivatives and analogs thereof can be used in combination with viral protease inhibitors, including but not limited to, Invirase (saquinavir, Roche), ABT-538 (Abbott, CAS Reg. No. 155213-67-5), AG1343 (Burroughs Wellcome/Glaxo, CAS Reg. No. 161814-49-9). Protease inhibitors are generally thought to work primarily during or after assembly (i.e., viral budding) to inhibit maturation of virions to a mature infectious state. For example, ABT-538 has been shown to have potent antiviral activity in vitro and favorable pharmokinetic and safety profiles in vivo (Ho, et al., 1995, Nature 373:123–126). Administration of ABT-538 to AIDS patients causes plasma HIV-1 levels to decrease exponentially and CD4 lymphocyte counts to rise substantially. The exponential decline in plasma viraemia following ABT-538 treatment reflects both the clearance of free virions and the loss of HIV-1 producing cells as the drug substantially blocks new rounds of infection. ABT-538 treatment reduces virus-mediated destruction of CD4 lymphocytes. Combining this treatment with a preparation of reduced or absent pyrogenicity of LPS or lipid A or an analog or derivative thereof, which inhibits at an earlier stage of HIV infection, viral fusion, would be likely to have synergistic effects and have a dramatic clinical impact.

In order to evaluate potential therapeutic efficacy of reduced-pyrogenic or non-pyrogenic preparations of LPS or lipid A or derivatives and analogs thereof in combination with the antiviral therapeutics described above, these combinations may be tested for antiviral activity according to methods known in the art.

A compound of the invention can be administered to a human patient by itself or in pharmaceutical compositions where it is mixed with suitable carriers or excipients at doses to treat or ameliorate various conditions involving HIV-infection. A therapeutically effective dose further refers to that amount of the compound sufficient to inhibit HIV infection. Therapeutically effective doses may be administered alone or as adjunctive therapy in combination with other treatments for HIV infection or associated diseases. Techniques for the formulation and administration of the compounds of the instant application may be found in "Remington's Pharmaceutical Sciences" Mack Publishing Co., Easton, Pa., latest addition.

In another embodiment, HIV infection is treated or prevented by administration of a Therapeutic of the invention in combination with one or more chemokines. In particular, the Therapeutic is administered with one or more C—C type chemokines, especially one or more from the group RANTES, MIP-1α and MIP-1β).

5.5 Demonstration of Therapeutic Utility

The present invention relates to assaying the therapeutic compounds of the present invention for their therapeutic effectiveness, including assaying their pyrogenicity properties in addition to their ant-HIV properties Such assays include, but are not limited to:
5.4.1 Determining the Pyrogenicity of the Preparation The Therapeutics of the invention are preferably tested in vitro, and then in vivo for non-pyrogenicity or reduced pyrogenicity, prior to use in humans. Any in vitro or in vivo assay known in the art to measure pyrogenic, inflammatory or endotoxic activity can be used to test the pyrogenicity of a Therapeutic of the invention. By way of example, and not by way of limitation, one could use any of the in vitro assays described infra in Section 6.

In an embodiment of the invention, a method of screening a preparation comprising LPS or lipid A or a derivative or analog thereof for pyrogenic properties comprises assaying said preparation for the ability to induce secretion of pyrogenic cytokines. In one specific embodiment, the preparation comprising LPS or lipid A or a derivative or analog thereof is assayed by a method comprising measuring cytokine levels secreted from peripheral blood monocytes, which cells have been contacted with the preparation and comparing to levels of cytokines secreted from cells not contacted with the preparation and/or levels of cytokines secreted from cell contacted with *E. coli* LPS (known to be highly pyrogenic). Quantitation of TNFα, IL-1β or IL-6 in culture supernatants can be achieved by capture ELISA. In another specific embodiment, the preparation comprising LPS or lipid A or a derivative or analogue thereof is assayed by a method comprising measuring β chemokine levels secreted from peripheral blood monocytes, which cells have been contacted with the preparation and comparing to levels of β chemokines secreted from cells not contacted with the preparation and/or levels of chemokines secreted from cells contacted with *E. coli* LPS. Quantitation of MIP-1α, MIP- 1β and RANTES in culture supernatants can be achieved by capture ELISA.

The assays described above may be carried out by any method known in the art. By example, and not by limitation, the assays described above may be carried out as follows:

50 ml of whole blood is mixed with an equal volume of RPMI (Life Technologies) and PBMCs are isolated by density gradient using lymphocyte separation medium according to the manufacturer's directions (Organon). The PBMCs are washed twice with RPMI then resuspended in 6 ml of ice cold sterile water and placed on ice for 30 sec to lyse the erythrocytes. The osmolarity is adjusted by adding 2 ml of ice cold 3.5% (w/v) NaCl; the PBMCs are harvested by centrifugation, washed with RPMI and resuspended in complete medium (CM; RPMI containing pyruvate, glutamine, PenStrep, and 10% endotoxin-free human AB serum (Life Technologies) at a density of $6 \times 10^6$ PBMCs/ml. CM containing the preparations to be assayed are placed into duplicate wells of a 96-well flat bottom culture late (Costar) at double the target final concentration. An equal volume of CM containing the PBMCs then is added to these wells and the culture plates are incubated at 37° C. in 5% $CO_2$ for 8 hr. The supernatants are then removed and stored at 70° C.

Quantitation of TNFα, IL-1β, IL-6, MIP-1α, MIP-1β and RANTES in these culture supernatants is achieved by capture ELISA (R&D Systems).

The Therapeutics of the invention may also be tested in vivo for non-pyrogenicity prior to use in humans. For example, pyrogenic activity may be measured in vivo by a dermal Schwartzman reaction and the rabbit pyrogen test. By way of example but not limitation, this is performed as follows: New Zealand rabbits may receive an intradermal injection of the preparation of LPS or lipid A or a derivative or analog thereof (approximately 2.5 μg), followed by an intravenous dose (2–4 μg/kg) 24 hours later. The dermal lesions are scored 4 to 6 hours later and compared to rabbits which received an infection of a preparation of LPS from *E. coli*. The therapeutics of the invention may also be determined by the rabbit pyrogen test. The thermal response index (TRI) for LPS preparations is determined by injecting a New Zealand white rabbit weighing 3–4 kg with an intravenous dose of approximately 50 ng LPS. Temperature is monitored with a rectal probe and recorded every 10 minutes. The TRI is the integrated product of the temperature above baseline (0C) and time (degree-hours) (Zimmer et al., 1981 *Peptides* 2:413).

5.4.2 Determining the ANTI-HIV Activity of the Preparation

The Therapeutics of the invention are preferably tested in vitro, and then in vivo for the desired therapeutic or prophylactic activity, prior to use in humans. Any in vitro or in vivo assay known in the art to measure HIV infection or production can be used to test the efficacy of a Therapeutic of the invention. By way of example, and not by way of limitation, one could use any of the in vitro or in vivo assays described infra in Section 6.

In an embodiment of the invention, a method of screening a preparation comprising a lipopolysaccharide, i.e. lipid A or LPS or lipid A antagonist or LPS antagonist, having non-pyrogenic properties or any derivative or analogue thereof, for anti-HIV activity is provided, which assay comprises assaying said preparation for the ability to inhibit HIV replication or expression of HIV RNA or protein. In one specific embodiment, the lipopolysaccharide preparation is assayed by a method comprising measuring HIV-1 p24 antigen levels in cultured hematopoietic cells which have been contacted with the lipopolysaccharide preparation prior to infection with HIV-1, and comparing the measured HIV-1 p24 antigen levels in the cells which have been contacted with the lipopolysaccharide preparation with said levels in cells not so contacted with the preparation, wherein a lower level in said contacted cells indicates that the preparation has anti-HIV activity. In another specific embodiment, the lipopolysaccharide preparation is assayed by a method comprising measuring the activity of a reporter gene product expressed from a construct in which the HIV-1 LTR is operably linked to said reporter gene, wherein said construct is present in cells which have been contacted with the preparation; and comparing the measured expression of said reporter gene in the cells which have been contacted with the preparation with said levels in such cells not so contacted, wherein a lower level in said contacted cells indicates that the preparation has anti-HIV activity. In another specific embodiment, the lipopolysaccharide preparation is assayed by a method comprising measuring HIV-1 derived RNA transcripts or HIV-1 antigen levels in HIV-1 transgenic mice administered the preparation; and comparing the measured transcript or antigen levels in the mice which have been administered the preparation with said levels in mice not so administered, wherein a lower level in said administered mice indicates that the preparation has anti-HIV activity. In yet another specific embodiment, the lipopolysaccharide preparation is assayed by a method comprising measuring SIV p27 antigen levels in the peripheral blood mononuclear cells of SIV infected monkeys administered the preparation; and comparing the measured antigen levels in the monkeys which have been exposed to the preparation with said levels in monkeys not so administered, wherein a lower level in said administered monkeys indicates that the preparation has anti-HIV activity.

By way of example, to assay a Therapeutic in vitro, one can examine the effect of the Therapeutic on HIV replication in cultured cells. Briefly, cultured hematopoietic cells (e.g., primary PBMCs, isolated macrophages, isolated $CD4^+$ T cells or cultured H9 human T cells) are acutely infected with HIV-1 using titers known in the art to acutely infect cells in vitro, such as $10^5$ $TCID_{50}$/ml. Then, appropriate amounts of the Therapeutic are added to the cell culture media. Cultures are assayed 3 and 10 days after infection for HIV-1 production by measuring levels of p24 antigen using a commercially available ELISA assay. Reduction in p24 antigen levels over levels observed in untreated controls indicates the Therapeutic is effective for treatment of HIV infection.

Additionally, assays for HIV-1 LTR driven transcription are useful for testing the efficacy of Therapeutics of the invention. Specifically, a reporter gene, i.e., a gene the protein or RNA product of which is readily detected, such as, but not limited to, the gene for chloramphenicol acetyltransferase (CAT), is cloned into a DNA plasmid construct such that the transcription of the reporter gene is driven by the HIV-1 LTR promoter. The resulting construct is then introduced by transfection, or any other method known in the art, into a cultured cell line, such as, but not limited to, the human $CD4^+$ T cell line HUT78. After exposure of the transformed cells to the Therapeutic, transcription from the HIV-1 LTR is determined by measurement of CAT activity using techniques which are routine in the art. Reduction in HIV-1 LTR driven transcription demonstrates utility of the Therapeutic for treatment and/or prevention of HIV infection.

Exemplary tests in animal models are described briefly as follows: First, a Therapeutic of the invention is administered to mice transgenic for HIV-1, e.g., mice which have integrated molecular clone pNL4-3 containing 7.4 kb of the HIV-1 proviral genome deleted in the gag and pol genes (Dickie, P., et al., 1991, *Virology* 185:109–119). Skin biopsies taken from the mice are tested for HIV-1 gene expression by RT-PCR (reverse transcription-polymerase chain reaction) or for HIV-1 antigen expression, such as expression of gp120or NEF, by immunostaining. Additionally, the mice are examined for reduction in the cachexia and growth retardation usually observed in HIV-1 transgenic mice (Franks, R. R., et al., 1995, *Pediatric Res.* 37:56–63).

The efficacy of Therapeutics of the invention can also be determined in SIV infected rhesus monkeys (see Letrin, N. L., and King, N. W., 1990, *J. AIDS* 3:1023–1040), particularly rhesus monkeys infected with $SIV_{mac251}$, which SIV strain induces a syndrome in experimentally infected monkeys which is very similar to human AIDS (Kestler, H., et al., 1990, *Science* 248:1109–1112). Specifically, monkeys can be infected with cell free $SIV_{mac251}$, for example, with virus at a titer of $10^{4.5}$ $TCID_{50}$/ml. Infection is monitored by the appearance of SIV p27 antigen in PBMCs. Utility of the Therapeutic is characterized by normal weight gain, decrease in SIV titer in PBMCs and an increase in $CD4^+$ T cells.

Once the Therapeutic has been tested in vitro, and also preferably in a non-human animal model, the utility of the Therapeutic can be assayed in human subjects. The efficacy of treatment with a Therapeutic can be assessed by measurement of various parameters of HIV infection and HIV associated disease. Specifically, the change in viral load can be determined by quantitative assays for plasma HIV-1 RNA using quantitative RT-PCR (Van Gemen, B., et al., 1994, *J. Virol. Methods* 49:157–168; Chen, Y. H., et al., 1992, *AIDS* 6:533–539) or by assays for viral production from isolated PBMCs. Viral production from PBMCs is determined by co-culturing PBMCs from the subject with H9 cells and subsequent measurement of HIV-1 titers using an ELISA assay for p24 antigen levels (Popovic, M., et al., 1984, *Science* 204:309–25 321). Another indicator of plasma HIV-1 levels and AIDS progression is the production of inflammatory cytokines such as IL-6, IL-8 and TNF-α; thus, efficacy of the Therapeutic can be assessed by ELISA tests for reduction of serum levels of any or all of these cytokines. Administration of the Therapeutic can also be evaluated by assessing changes in $CD4^+$ T cell levels, body weight, or any other physical condition associated with HIV infection or AIDS or AIDS Related Complex (ARC). Reduction in HIV viral load or production, increase in $CD4^+$ T cell or amelioration of HIV-associated symptoms demonstrates utility of a Therapeutic for administration in treatment/prevention of HIV infection.

5.6 Therapeutic Compositions and Methods of Administration

The invention provides methods of treatment and prevention by administration to a subject in need of such treatment of a therapeutically or prophylactically effective amount of a Therapeutic of the invention. The subject is preferably an animal, including, but not limited to, animals such as primates, monkeys, cows, pigs, horses, chickens, cats, dogs, etc., and is preferably a mammal, and most preferably human. In a specific embodiment, the subject is a human afflicted with HIV infection or related disorders. In a preferred embodiment, the Therapeutic is purified (i.e., separated from components with which it is associated in its natural environment).

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, *J. Biol. Chem.* 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, N.Y., pp. 353–365 (1989); Lopez-Berestein, ibid., pp. 317–327; see generally ibid.) In yet another embodiment, the Therapeutic can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Florida (1974); *Controlled Drug Bioavailability, Drug Product Design and Performance*, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see, e.g., Goodson, in *Medical Applications of Controlled Release*, supra, vol. 2, pp. 115–138 (1984)).

Other controlled release systems are discussed in the review by Langer (*Science* 249:1527–1533 (1990)).

The present invention also provides pharmaceutical compositions. Such compositions comprise a therapeutically effective amount of a Therapeutic, and a pharmaceutically acceptable carrier. As used herein, the term "pharmaceutically acceptable carrier" refers to a carrier medium that does not interfere with the effectiveness of the biological activity of the active ingredient, is chemically inert and is not toxic to the patient to whom it is administered. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances. Predicted suitable doses of a non-pyrogenic preparation of LPS or lipid A or derivatives or analogs thereof for treatment or prevention of HIV infection include, but are not limited to, 1 ng/kg to 2 mg/kg per week. Routes of administration of a Therapeutic include, but are not limited to, intramuscularly, subcutaneously or intravenously. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

NON-PYROGENIC LPS STIMULATES β CHEMOKINE SECRETION IN PBMC

These experiments were carried out to demonstrate the ability of non-pyrogenic LPS antagonists to competitively inhibit the interaction between LPS and the cellular receptor for LPS. Recent biochemical evidence suggests that the htrB and msbb genes serve as lauroyl and myristoyl transferases, respectively (Rietschel et al., 1994 *FASEB J*. 8:217–225; Summerville et al., 1996, *J. Clin. Invest*. 97: 359–365; Lee et al., 1995, *J. Biol. Chem*. 270:27151–27159). In support, mass spectrometry analysis of LPS from an *E. coli* msbB mutant showed that this mutant produced a pentaacyl lipid A that lacked the ester-linked myristoyl side chain (Lee et al., supra). Similarly, an htrB mutant of *Haemophilus influenzae* produced a mixture of pentaacyl and tetraacyl lipid A. Thus, HtrB and MsbB transferase activities are believed to be necessary for the generation of LPS from $KDO_2$-lipid $IV_A$ (Summerville et al., supra). These experiments tested whether an *E. coli* htrB msbB double mutant would accumulate LPS that contained lipid A partial structures and that would serve as a convenient source of LPS antagonist.

6.1 Materials and Methods

Cell Culture

Strains W3110 and MLK986 were cultured on solid media both at 30° C., 37° C. or 42° C. prior to seeding the liquid media. Liquid cultures (1L) were seeded the following day at a starting inoculum of ca. $1 \times 10^4$ cfu/ml and grown for 16 hr at 30° C., 37° C. or 42° C. with shaking (250 opm).

Isolation of LPS

The liquid cultures were harvested by centrifugation at 7000×g for 10 min, washed once in 250 ml endotoxin-free irrigation saline (Baxter) and the weight of the bacterial pellets was determined. The pellets then were resuspended in endotoxin-free water (Baxter) at a final density of 2% w/v±0.25%. Subsequently, LPS was isolated by two cycles of hot-water phenol extraction. In short, the bacterial suspensions were heated to 70° C. to which an equal volume of pre-warmed phenol was added and mixed for 15 min at 70°

C. The mixtures were cooled to 25° C. and then centrifuged at 18,000×g for 15 min. Following this centrifugation the aqueous phases were removed, placed into dialysis tubing (SpectraPor) and dialyzed against running distilled $H_2O$ overnight. The retentates were then placed into fresh 50 ml polypropylene tubes and treated with RNaseA (100 μg/ml) at 37° C. for 1 hr, followed by DNaseI (50 μg/ml and 5 mM $Mgcl_2$) at 37° C. for 1 hr, followed by Pronase (250 μg/ml) at 37° C. for 1 hr. Then EDTA was added to a final concentration of 5 mM and the hot-water phenol extraction procedure described above was repeated. Following dialysis the retentates were centrifuged at 20,000×g for 15 min at 4° C. The supernatants were transferred to fresh Beckman 50Ti tubes and the LPS was pelleted by centrifugation at 110,000×g for 2H at 4° C. The supernatants were discarded and the pellets were vacuum dried. Each LPS preparation was evaluated for DNA and protein contamination by SDS-PAGE and silver stain, BCA protein estimate assay and UV spectrophotometry.

PBMC Activation Assays

PBMCs were obtained from 50 ml of whole blood as described above and resuspended in complete medium (CM; RPMI containing pyruvate, glutamine, PenStrep, and 10% endotoxin-free human AB serum (Life Technologies) at a density of $6 \times 10^6$ PBMCs/ml. CM containing W3110 LPS, MLK986 LPS or synthetic lipid $IV_A$ was placed into duplicate wells of a 96-well flat bottom culture late (Costar) at double the target final concentration. An equal volume of CM containing the PBMCs then was added to these wells and the culture plates were incubated at 37° C. in 5% $CO_2$ for 8 hr. The supernatants were then removed and stored at 70° C. Quantitation of TNFα, IL-1β, IL-6, MIP-1α and MIP-1β in these culture supernatants was achieved by capture ELISA (R&D Systems).

6.2 RESULTS

LPS was extracted from *Escherichia coli* strain W3110 and a htrB1::Tn10, msbB::Ωcam double mutant derivative of W3110, strain MLK986 (Karrow et al., 1992, *J. Bacteriol* 174:702–710) after culturing them at 30° C., 37° C. or 42° C. as described (Westphal et al., 1965, *Met. Carbohyd. Res.* 5:83–91). To characterize the proinflammatory activity of LPS harvested from W3110 and MLK986 bacilli cultured at over this temperature range, we measured the level of TNFα in culture supernatants 8 hr after stimulation of human PBMCS. The results showed that significant levels of TNFα secretion was induced by parent strain W3110 LPS at concentrations above 1 ng/ml, irrespective of culture temperature (FIG. 1). In contrast, LPS from mutant strain MLK986 cultured at 30° C. only modestly elicited TNFα secretion and LPS derived from MLK986 bacilli cultured at 37° C. and 42° C. even at concentrations as high as 1 μg/ml did not elicit significant TNFα secretion in the human PBMC activation assay (FIG. 1). This observation was reproduced using four unrelated PBMC donors and two separate LPS preparations. In addition, a similar secretion pattern was seen for IL-1β in the culture supernatants of PBMCs after stimulation with each of the MLK986 and W3110 LPS preparations (Table 1). Secretion of IL-6 was more variable from PBMC donor to PBMC donor. In some instances LPS from MLK986 cultured either at 37° C. or 42° C. induced a modest increase in IL-6 (Table 1). However, the levels were similar to the level of IL-6 induced by non-pyrogenic synthetic lipid $IV_A$ (ICN) and were 5-fold lower than the level of IL-6 induced by 100-fold less W3110 LPS (Table 1). We believe these data indicate that LPS isolated from MLK986 cultured at or above 37° C. possesses negligible proinflammatory activity.

TABLE 1

Levels of IL-1β and IL-6 in human PBMC culture supernatants after stimulation with LPS

| LPS source (Culture Temperature) | IL-1β (pg/ml) | IL-6 (pg/ml) |
| --- | --- | --- |
| None | 12 ± 1 | 2296 ± 43 |
| W3110 (37° C.) (10 ng/ml) | 7032 ± 366 | 30,698 ± 120 |
| MLK986 (30° C.) (1 μg/ml) | 1918 ± 182 | 16,000 ± 26 |
| MLK986 (37° C.) (1 μg/ml) | 12 ± 3 | 7593 ± 221 |
| MLK986 (42° C.) (1 μg/ml) | 11 ± 4 | 5164 ± 144 |
| Lipid $IV_A$ (42° C.) (1 μg/ml) | 13 ± 1 | 7581 ± 20 |

To investigate whether MLK986 LPS possesses LPS antagonist activity, MLK986 LPS (cultured at 37° C.) at 1 μg/ml was mixed with varying amounts of W3110 LPS (also cultured at 37° C.) from 1 ng/ml to 100 ng/ml and these mixtures were used to stimulate human PBMCs as outlined above. W3110 LPS (also cultured at 37° C.) from 1 ng/ml to 100 ng/ml alone and W3110 LPS (10 ng/ml) mixed with synthetic lipid $IV_A$ (1 μg/ml) were used as controls. The level of TNFα in culture supernatants collected 8 hr after stimulation shows that W3110 LPS at a concentration of 1 ng/ml and above elicited TNFα secretion but that MLK986 LPS significantly antagonized this response (Table 2). Interestingly, LPS from MLK986 cultured at 42° C. produced did not display LPS antagonist activity. Since culture temperature has been shown to influence LPS aggregation and influence LPS activity (Shnyra et al., 1993, *Infection and Immunity* 61:5351–5360), this later finding may be due to differential aggregation properties of MLK986 LPS produced under the distinct culture conditions.

TABLE 2

LPS antagonist properties of MLK986 LPS

| Treatment | TNFα (pg/ml) |
| --- | --- |
| W3110 (100 ng/ml) | 1404 ± 40 |
| W3110 (10 ng/ml) | 1192 ± 37 |
| W3110 (1 ng/ml) | 536 ± 178 |
| MLK986/37° C. (1 μg/ml) | <30 |
| MLK986/37° C. (1 μg/ml) + W3110 (100 ng/ml) | <30 |
| MLK986/37° C. (1 μg/ml) + W3110 (10 ng/ml) | <30 |
| MLK986/37° C. (1 μg/ml) + W3110 (1 ng/ml) | <30 |
| Lipid $IV_A$ (1 μg/ml) + W3110 (10 ng/ml) | <30 |

In light of the growing importance of β chemokines in microbial infection (Murphy, 1994, *Ann. Rev. Immunol.* 12:593–633; Cocchi et al. 1955, *Science* 270:1811–1815), we investigated whether LPS from MLK986 or RSDPLA were capable of eliciting MIP-1α, MIP-1β or RANTES secretion from human PBMCs in vitro. Human PBMCs were stimulated with various doses MLK986 LPS or RSD-PLA (Kitchens et al. 1992, *J. Exp. Med.* 176:485–494) and the levels of MIP-1α, MIP-1β or RANTES in the culture supernatants 8, 16, 24, and 48 hr after stimulation were determined by quantitative capture ELISA (R&D Systems).

Reproducibly, we found that LPS from MLK986, cultured at either 37° C. or 42° C., and RsDPLA stimulated the secretion of MIP-1α and MIP-1β in a dose-dependent manner (FIG. 2); the peak production of these chemokines occurred 24 hr after stimulation (FIG. 3).

6.3 Discussion

In this example, we presented the novel finding that LPS antagonists, both *E. coli* mutant LPS and R. sphaeroides diphosphoryl lipid A (RsDPLA), possess subtle biological activity in a human PBMC activation assay. The ability of these LPS antagonists to elicit MIP-1α and MIP-1β is inconsistent with a passive competitive inhibition model and therefore suggests a more complicated mechanism. Irrespective of the basis for this response, the observation that β chemokines MIP-1α and MIP-1β secretion can be elevated in the absence of endogenous pyrogenic cytokines such as TNFα and IL-1β can open new avenues for novel therapeutic strategies that exploit this host response.

7. EXAMPLE

INHIBITION OF HIV-1 REPLICATION IN HUMAN PBMC-DERIVED MONOCYTES BY NON-PYROGENIC LPS

The following studies were conducted to demonstrate that non-pyrogenic LPS isolated from *E. coli* htrB1::Tn10 msbB::Ωcam double mutant MLK986 is capable of inhibiting HIV replication in human cells.

7.1 Method

Isolation of PBMCS and monocyte-derived macrophages. PBMC healthy donors were placed in 24 well plates at $3 \times 10^6$ cells/ml in 1 ml of growth medium (GM) (RPMI-1640+10% FBS+10% human serum+Penn/Strep). Monocytes which had been isolated by negative selection with magnetic beads to remove T and B cells, were place in a 25 cm$^2$ flask and further purified by adherence to the flask. After washing, the monocytes were cultured in GM as above.

7.2 Results

Induction of β chemokines. These cultures were then treated with the LPS preparations as indicated. After 24 hours the supernatants were collected from each these cultures and the level of β-chemokines and TNF-α and IL-1β were measured by ELISA (R&D Systems). The data shown in Table 3 are representative of 3 different experiments, and indicate that both MLK986 and wild type LPS induce comparable levels of β-chemokines in macrophages and PBMC cultures. However, in contrast to wild type LPS, MLK986 LPS did not induce a measurable TNF-α response.

Inhibition of HIV-1 infection. Monocyte-derived macrophages were treated with the LPS preparations (1 µg/ml) and then infected with HIV-1$_{Ba-L}$ at 0.5 ng/ml for 3 hours, washed with PBS 4 times, and cultured in growth medium for days. Supernatants were collected at days 4, 7, and 10 days post-infection, and tested for the presence of p24 antigen by ELISA (Coulter). Representative data from 3 different experiments (Table 4) show that both MLK986 and wild type LPS potently inhibit HIV-1 replication in monocyte-derived macrophages. In addition, pretreatment of human PBMCs with supernatants collected 24 hr after stimulation of PBMC with various LPS preparations inhibited HIV-1 infection (Table 5). The data shown in FIG. 4A are representative of 4 different experiments and demonstrate that MLK986/37 inhibits HIV-1 chemokines. Thus, MLK986/37 induced HIV-1 inhibition in MDM is reversed by addition of a mixture of neutralizing antibodies against RANTES, MIP-1α, and MIP-1β (from R&D Systems Inc.; 200 ug/ml each) (FIG. 4B). Further, HIV-1 replication inhibition occurred without inducing pyrogenic cytokines (FIG. 4C). These results clearly demonstrate that the LPS antagonist MLK986/37 notently inhibits HIV-1 replication.

TABLE 3

Levels of β-chemokines and TNF-α in PBMC culture supernatants after 24 hours of LPS stimulation (1 mg/ml).

| LPS source | RANTES ng/ml | MIP-1α ng/ml | MIP-1β ng/ml | TNF-α ng/ml |
| --- | --- | --- | --- | --- |
| none | 0.212 +/− .030 | 0.170 +/− .008 | 0.416 +/− .052 | <30 |
| LPS wt | 2.65 +/− 1.98 | 9.22 +/− 1.38 | 6.76 +/− .580 | 1.96 +/− .969 |
| MLK986 (Prep. P) | 2.489 +/− 1.93 | 8.84 +/− .830 | 6.72 +/− .587 | <30 |

TABLE 4

HIV-1 p24 expression in macrophages pretreated with LPS.

| LPS source | Day 4 | Day 7 | Day 10 |
| --- | --- | --- | --- |
| none | .340 +/− .095 | .890 +/− .153 | 1.64 +/− .562 |
| LPS wt | .018 +/− .006 | 27 +/− .0014 | .035 +/− .005 |
| MLK986 (Prep. 02) | .027 +/− .012 | .051 +/− .025 | .01 +/− .032 |

TABLE 5

HIV-1 p24 expression in PBMC pretreated with supernatants from PBMC stimulated with MLK986, wild type LPS (*E. coli*, SIGMA) (both at 1 mg/ml) or control.

| LPS source | Day 4 | Day 7 |
| --- | --- | --- |
| none | .889 +/− .068 | 2.03 +/− .158 |
| LPS wt | .039 +/− .032 | .081 +/− .033 |
| MLK986 | .094 +/− .067 | .134 +/− .038 |

8. EXAMPLES

SYNTHETIC LIPID IV$_A$ SUPPRESSES HIV REPLICATION WITHOUT INDUCING MEASURABLE LEVELS OF β CHEMOKINES

The following studies were conducted to demonstrate that non-pyrogenic LPS antagonist lipid IV$_A$ is capable of inhibiting HIV replication in human cells.

8.1 Methods and Results

To investigate the utility of the aforementioned findings, we investigated whether commercially available synthetic lipid IV$_A$ (ICN Inc.) suppressed the replication of HIV-1$_{BAL}$ in human PBMC-derived monocytes. Therefore, PBMCs were obtained as outlined in Section 6, see above, and placed into 12 well culture flat-bottom plate and incubated in CM (see example 1) for 12 days at 37° C. in 5% CO$_2$. Non-adherent cells were removed and the cells were given fresh media every 2 days. After 6 days, the adherent PBMCs were treated with synthetic lipid IV$_A$ at 1000 ng/ml, 100 ng/ml and 10 ng/ml for 24 hours. The treated cells were subsequently infected with 0.200 ng of HIV-1$_{BAL}$ (Cocchi et al, supra) for 2 hours, washed twice and incubated for a further 19 days. Culture supernatants were then collected and the level of p24 in these supernatants was measured by ELISA (R&D Systems). The results of this assay show that lipid $IV_A$ suppresses the replication of HIV-$1_{BAL}$ in a dose-dependent manner (FIG. 5). These results provide clear evidence that synthetic LPS antagonists, such as lipid $IV_A$, are capable of suppressing HIV replication over a wide range of concentrations.

9. EXAMPLES

NON-PYROGENIC LPS SUPPRESSES HIV REPLICATION WITHOUT DISPLAYING LPS ANTAGONIST ACTIVITY

The following studies were conducted to demonstrate that non-pyrogenic LPS isolated from E. coli htrB1::Tn10 msbB::Ωcam double mutant MLK986 cultured at 42° C. is capable of inhibiting HIV replication in human cells. 9.1 Methods and Results We investigated whether LPS isolated from MLK986 cultured at 42° C. (MLK986/42) suppressed the replication of HIV-$1_{BAL}$ in human PBMC-derived monocytes. This LPS preparation induces lower levels of β chemokines that LPS isolated from MLK986 cultured at 37° C. and did not display LPS antagonist activity (see above). PBMC-derived monocytes were obtained as outlined in Section 8, see above. After 6 days, the PBMC-derived monocytes were treated with MLK986/42 at 1000 ng/ml, 100 ng/ml and 10 ng/ml for 24 hours. The treated cells were subsequently infected with 0.200 ng of HIV-$1_{BAL}$ (Cocchi et al., supra) for 2 hours, washed twice and incubated for a further 19 days. Culture supernatants were then collected and the level of p24 in these supernatants was measured by ELISA (R&D Systems). The results of this assay show that MLK986/42 suppresses the replication of HIV-$1_{BAL}$ in a dose-dependent manner.

This example provides direct evidence that non-pyrogenic LPS preparations that lack LPS antagonist properties, such as MLK986/42, are capable of suppressing HIV replication over a wide range of concentrations.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An in vitro method of reducing human immunodeficiency virus (HIV-1) replication in monocytes comprising introducing to the monocytes a composition comprising a variant lipopolysaccharide (LPS) component in an amount effective to reduce HIV replication therein, wherein the variant LPS is an isolated and purified LPS component obtained from a double mutant E. coli which is designated E coli htrB1::Tn10 msbB::Ωcam strain having ATCC Accession No. PTA-2794, wherein the LPS component has the following properties:
   (a) exhibits reduced pyrogenicity relative to a wild-type E. coli lipopolysaccharide;
   (b) stimulates β chemokine secretion from the mononuclear cells;
   (c) reduces secretion of TNF-α proinflammatory relative to a wild-type E. coli lipopolysaccharide; and
   (d) reduces replication of HIV in the monocytes.

2. The method of claim 1 which further comprises administering to the subject a therapeutically effective amount of a chemokine.

3. The method of claim 2 which further comprises administering to the subject a therapeutically effective amount of a chemokine selected from the group consisting of RANTES, MIP-1α and MIP-1β.

4. The method of claim 1 which further comprises combining the variant LPS with an anti-viral drug.

5. The method of claim 4 in which the anti-viral drug is selected from one or more of the group consisting of AZT, 3TC, ddI, ddC, 3TC, and sequinavir.

6. The method of claim 4 in which the anti-viral drug is selected from a protease inhibitor or a glycosylation inhibitor.

7. The method of claim 1 further comprising combining the variant LPS with a pharmaceutically acceptable carrier.

8. The method of claim 1 wherein said composition further comprises a wild-type lipopolysaccharide containing structure isolated from a gram-negative microorganism.

9. An in vitro method of reducing human immunodeficiency virus (HIV-1) replication in monocytes, comprising administering to mononuclear cells a composition comprising a variant lipopolysaccharide (LPS) in an amount effective to reduce HIV replication, wherein the variant LPS has been isolated/purified from an E. coli double mutant htrB1::Tn10 msbB::Ωcam strain having ATCC Accession No. PTA-2794, and having the following properties:
   (a) exhibits reduced pyrogenicity relative to a wild-type E. coli lipopolysaccharide;
   (b) induces secretion of one or more β-chemokines selected from the group consisting of RANTES, MIP-1α and MIP-1β;
   (c) reduces secretion of one or more pro-inflammatory cytokines selected from the group consisting of TNFα, IL-1β and IL-6 relative to a wild-type E. coli lipopolysaccharide; and
   (d) reduces HIV replication in monocytes.

10. The method of claim 9 further comprising combining the variant LPS with an anti-viral drug other than a lipopolysaccharide variant of reduced or absent pyrogenicity.

11. The method of claim 9 further comprising combining the variant LPS with a pharmaceutically acceptable carrier.

12. The method of claim 6, wherein the anti-viral drug comprises a nucleoside derivative.

13. The method of claim 9, wherein said composition further comprises a wild-type lipopolysaccharide containing structure isolated from a gram-negative microorganism.

14. The method of claim 9, wherein the composition further comprises a nucleoside derivative.

15. The method of claim 14, where the nucleoside is selected from the group consisting of a modified purine nucleoside, a modified pyrimidine and halogenated nucleoside derivative.

16. The method of claim 1 wherein the reduction of HIV replication is determined by measuring HIV-1 p24 antigen levels.

17. The method of claim 12, wherein the nucleoside is selected from the group consisting of a modified purine nucleoside, a modified pyrimidine and halogenated nucleoside derivative.

* * * * *

UNITED STATES PATENT AND TRADEMARK OFFICE
CERTIFICATE OF CORRECTION

PATENT NO. : 6,841,345 B1
DATED : January 11, 2005
INVENTOR(S) : Hone et al.

It is certified that error appears in the above-identified patent and that said Letters Patent is hereby corrected as shown below:

Column 2,
Line 50, "MIP-1a" should be -- MIP-1α --

Column 6,
Line 14, "he" should be -- the --

Column 10,
Lines 9, 17, 22 (both occurrences) and 27, "htrb" should be -- htrB --

Column 13,
Line 1, "$C_2$-$C_{20}$" should be -- $C_{2-20}$ --

Column 19,
Line 29, "orlipid" should be -- or lipid --

Column 25,
Line 7, "gp120or" should be -- gp120 or --
Line 38, "204:309-25 321)" should be -- 204:309-321) --

Column 28,
Line 36, "msbb" should be -- msbB --

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,841,345 B1 | Page 1 of 1 |
| APPLICATION NO. | : 09/383709 | |
| DATED | : January 11, 2005 | |
| INVENTOR(S) | : Hone et al. | |

It is certified that error appears in the above-identified patent and that said Letters Patent is hereby corrected as shown below:

STATEMENT OF GOVERNMENT RIGHTS

Col. 1 Line 1-4 insert
The United States Government has rights in this invention under Department of Health and Human Services Grant No. PAR-97-042.

Signed and Sealed this

Twenty-eighth Day of August, 2007

JON W. DUDAS
*Director of the United States Patent and Trademark Office*